United States Patent [19]

Newman et al.

[11] Patent Number: 5,792,775
[45] Date of Patent: Aug. 11, 1998

[54] 4' AND 4',4"-SUBSTITUTED-3-α-(DIPHENYLMETHOXY) TROPANE ANALOGS AS COCAINE THERAPEUTICS

[75] Inventors: Amy Hauck Newman, Phoenix. Md.; Andrew C. Allen, Exton, Pa.; Richard H. Kline, Owings Mills, Md.; Sari Izenwasser, Baltimore, Md.; Jonathan L. Katz, Columbia, Md.

[73] Assignee: The United States of America as represented by the Department of Health and Human Services, Washington, D.C.

[21] Appl. No.: 667,024

[22] Filed: Jun. 20, 1996

Related U.S. Application Data

[60] Provisional application No. 60/000,378 Jun. 21, 1995.

[51] Int. Cl.[6] .................... C07D 221/22; A61K 31/435
[52] U.S. Cl. ............................................ 514/299; 546/112
[58] Field of Search ........................... 546/112; 514/299

[56] References Cited

FOREIGN PATENT DOCUMENTS

| 1584088 | 12/1969 | France . |
| 1166798 | 10/1969 | United Kingdom . |
| WO 91/11184 | 8/1991 | WIPO . |
| WO 94/04146 | 3/1994 | WIPO . |

OTHER PUBLICATIONS

Hassan, J Pharm Pharmacol, vol 36, pp 7–10, 1984.
Reith, J of pHarm and Exp therap, vol. 271(3), pp. 1444–1452, 1994.
Xu, Biochem Pharm, vol. 49(3), pp. 339–350, 1995.
Roos, J of Chromatog, vol. 370, pp. 403–418, 1986.
Newman, J Med Chem, vol. 38, pp. 3933–3940, 1995.
Newman, J Med Chem, vol. 37, pp. 2258–2261, 1994.
Akunne, J of Pharm and Exp Therap, vol. 268(3), pp. 1461–141475, 1994.
Horn, Mol Pharm, vol. 7, pp. 66–80, 1971.
Acri, et al., *In Problems of Drug Dependance 1993* (Harris, L.S., Ed.; NIDA: Washington, DC, 1994; p. 441).
Brownell, et al., *Intl. J. Imaging Syst. Tech.*, 1:207–217 (1989).
Carroll, et al., *J. Med. Chem.*, 35:969–981 (1992).
Carroll, et al., *J. Chem. Soc., Chem. Commun.*, pp. 44–46 (1993).
Carroll, et al., *Med. Chem. Res.*, 3:468–472 (1993).
Cline, et al., *Behav. Pharmacol.*, 3:113–116 (1992).
Cline, et al., *J. Pharmacol. Exp. Ther.*, 260:1174–1179 (1992).
Coleman, et al, *Invest. Radiol.*, 21:1 (1986).
Coyle, et al., *Science*, 166:899–901 (1969).

D'Amato, et al., *J. Pharmaco. Exp. Ther.*, 242:364–371 (1987).
Davies, et al., *Eur. J. Parhacol. Mol. Pharmacol. Sect.*, 244:93–97 (1993).
Hammer, et al., *Life Sci.*, 38:1653–1662 (1986).
Izenwasser, et al., *Brain Res.*, 520:303–309 (1990).
Izenwasser, et al., *Eur. J. Pharmacol.*, 263:277–283 (1994).
Jaszczak, et al., *Ivest. Radiol.*, 20:897 (1985).
Katz, et al., *Soc. for Neuroscience Abstracts*, 20:1628 (1994).
Koe, *J. Pharmacol. Erp. Ther.*, 199:649–661 (1976).
Kozikowski, et al., *J. Med. Chem.*35:5764–4766 (1992).
Kuhar, et al., *Trends Neurosci.*14:299–301 (1991).

(List continued on next page.)

*Primary Examiner*—C. Warren Ivy
*Assistant Examiner*—D. Margaret M. Mach
*Attorney, Agent, or Firm*—Townsend and Townsend and Crew LLP

[57] ABSTRACT

The present invention provides a family of tropane analogs. More particularly, the present invention provides a family of 4' and 4',4"-substituted-3α-(diphenylmethoxy)tropane analogs having the formula

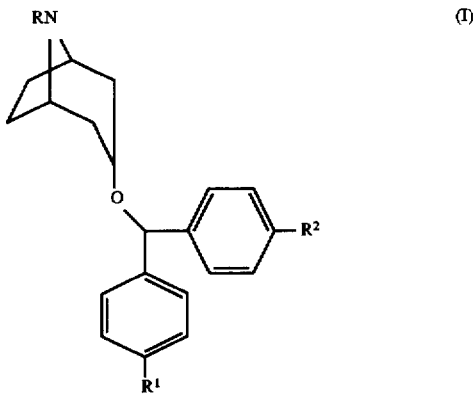

in which R is a functional group including, but not limited to, hydrogen, alkyl, alkoxy, arylalkyl, aryloxyalkyl, cinnamyl and acyl; and $R^1$ and $R^2$ are independently selected and are functional groups including, but not limited to, hydrogen, alkyl, alkoxy, hydroxy, halogen, cyano, amino and nitro. The benztropine analogs of the present invention have a high affinity for the dopamine transporter and inhibit dopamine uptake, but they do not exhibit a cocaine-like behavioral profile. Moreover, the present invention provides methods of using such benztropine analogs to treat cocaine abuse, to image dopamine transporter/cocaine binding sites, and to diagnose and/or monitor neurodegenerative disorders (e.g., Parkinson's disease). In addition, the present invention provides pharmaceutical compositions comprising a benztropine analog of the present invention and a pharmaceutically acceptable carrier or excipient.

20 Claims, 11 Drawing Sheets

OTHER PUBLICATIONS

Lewin, et al., *J. Med. Chem.*, 35:135–140 (1992)

Madras, et al., *CPDD 1994 Annual Scientific Meeting Abstracts*.

Madras, et al., *Mol. Pharmacol.*, 36:518–524 (1989).

Madras, et al., *Soc. for Neuroscience Abstracts*, 20:1625 (1994).

McKearney, *Psychopharmacology*, 78:377–379 (1982).

Meltzer, et al., *CPDD 1994 Annual Scientific Meeting Abstracts*.

Meltzer, et al., *J. Med. Chem.*, 37:2001–2010 (1994).

Newman, et al., *Soc. for Neuroscience Abstracts*, 19:1842 (1993).

Patlak, et al., *Blood Flow Metab.*, 5:584 (1986).

Raisman, et al., *Eur. J. Pharmacol.*, 78:345–351 (1982).

Ritz, et al., *Science*, 237:1219–1223 (1987).

Rothman, et al., *Life Sci. Pharmacol. Ltt.*, 46:PL–17–PL–21 (1990).

Van der Zee, et al., *Neuropharmacology*, 17:483–490 (1978).

Van der Zee, et al., *Eur. J. Med. Chem.*, 15:363–370 (1980).

Watson, *J. Pharmacol. Exp. Ther.*, 237:419–427 (1986).

Witkin, et al., *J. Pharmacol. Exp. Ther.*, 257:706–713 (1991).

4' AND 4',4"-SUBSTITUTED-3-α-(DIPHENYLMETHOXY) TROPANE ANALOGS AS COCAINE THERAPEUTICS

FIELD OF THE INVENTION

The present invention relates generally to a family of tropane analogs. More particularly, the present invention relates to a family of 4' and 4',4"-substituted-3α-(diphenylmethoxy)tropane analogs which have a high affinity for the dopamine transporter and inhibit dopamine uptake, but which do not exhibit a cocaine-like behavioral profile. In addition, the present invention relates to the use of such benztropine analogs to treat cocaine abuse, to image dopamine transporter/cocaine binding sites, and to diagnose and/or monitor neurodegenerative disorders (e.g., Parkinson's disease).

BACKGROUND OF THE INVENTION

The significant public health and social problems resulting from cocaine (compound 1 in FIG. 1) abuse have stimulated research efforts directed toward elucidating the central mechanisms by which cocaine exerts its behavioral effects. The data from these studies suggest that the primary mechanism of the behavioral effects of cocaine appears to be related to the inhibition of dopamine uptake (see, Ritz, M. C., et al., Science, 1987, 237, 1219–1223; and Kuhar, M. J., et al., Trends Neurosci. 1991, 14, 299–301) which results in an elevated concentration of dopamine in the synapse. As a consequence, considerable emphasis has been directed toward the dopamine transporter as a target for pharmacological tools for research and potential therapeutics for the treatment of cocaine abuse.

Systematic structure-activity relationships for a large series of cocaine analogs have primarily been provided by Carroll and colleagues (see, e.g., Carroll, F. I., et al., J. Med. Chem. 1992, 35 969–981). Recently, attention has been focused on the importance and functionality of the 2-position on the tropane ring (see, e.g., Kozikowski, A. P., et al., J. Med. Chem. 1992, 35, 4764–4766; Davies, H. M. L., et al., Eur. J. Pharmacol. Mol. Pharmacol. Sect. 1993, 244, 93–97; Carroll, F. I., et al., J. Chem. Soc., Chem. Commun. 1993, 44–46; and Carroll, F. I., et al., Med. Chem. Res. 1993, 3, 468–472). The original work by Lewin, et al. suggested that a 2β-ester or an equivalent thereof was necessary for high-affinity binding to the cocaine recognition site (See, J. Med. Chem. 1992, 35, 135–140). Small alkyl ketones in the 2β-position resulted in highly potent and enzymatically stable cocaine analogs (see, Davies, et al., supra, 1993). However, replacement of the 2β-methyl ester with a vinyl group resulted in potent cocaine analogs and argued against the proposal that hydrogen bonding at this position is important, as previously postulated (see, Kozikowski, A. P., et al., supra, 1992; Carroll, F. I., et al., supra, 1992; and Lewin, A., et al., supra, 1992).

In addition, attention has been focused on benztropine (compound 2 of FIG. 1). Benztropine, i.e., 3α-(diphenylmethoxy)-1αH,5αH-tropane is a dopamine uptake inhibitor, equipotent to cocaine, that exhibits CNS stimulatory activity in animal models (see, van der Zee, P., et al., Neurophannacology 1978, 17, 483–490; van der Zee, P., et al., Eur. J. Med. Chem. 1980, 15, 363–370; Coyle, J. T. and S. H. Snyder, Science 1969, 166, 899–901; Koe, B. K., J. Pharmacol. Exp. Ther. 1976, 199, 649–661; and McKearney, J. W., Psychopharmacology 1982, 78, 377–379; and Acri, J. B., et al., In Problems of Drug Dependence 1993 (Harris, L. S., Ed.; NIDA Monograph 141; NIDA: Washington, D.C., 1994; p 441)). The combination of a tropane ring, as found in cocaine, with the diphenylether function, as found in the potent series of aryl 1,4-dialkyl(en)-ylpiperazine dopamine uptake inhibitors, i.e., GBR 12909 (compound 3 of FIG. 1), have made benztropine an interesting template for the design of dopamine uptake inhibitors (see van der Zee, P., et al., supra, 1980).

Although a considerable amount of research has been carried out in an effort to develop cocaine analogs, there still remains a need in the art for novel tropane analogs which can be used to elucidate the mechanism by which cocaine alters behavior and which can be used as therapeutics in the treatment of cocaine abuse.

SUMMARY OF THE INVENTION

The present invention provides a family of tropane analogs. More particularly, the present invention provides a family of 4' and 4',4"-substituted-3α-(diphenylmethoxy) tropane analogs having the formula

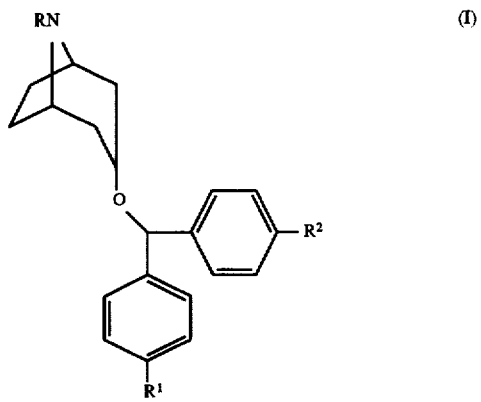

in which R is a functional group including, but not limited to, hydrogen, alkyl, alkoxy, arylalkyl, aryloxyalkyl, cinnamyl and acyl; and $R^1$ and $R^2$ are independently selected and are functional groups including, but not limited to, hydrogen, alkyl, alkoxy, hydroxy, halogen, cyano, amino and nitro.

The benztropine analogs of the present invention have a high affinity for the dopamine transporter and inhibit dopamine uptake, but they do not produce stimulation of locomotor activity or cocaine-like subjective effects in a drug discrimination model. Such properties are surprising from a number of different standpoints. First, all of the potent dopamine uptake inhibitors which have been evaluated behaviorally to date demonstrate these cocaine-like behavioral actions. Second, the structure-activity relationships for the benztropine analogs of the present invention differ considerably from cocaine and its structural analog, GBR 12909. For example, the benztropine analogs of the present invention are not substituted at the 2-position as are all of the potent cocaine analogs reported to date. In fact, none of the benztropine analogs of the present invention have a substituent in the 2-position, which has previously been deemed necessary for high affinity binding of the cocaine analogs to the dopamine transporter. Third, the benzhydryl ether moiety prefers the axial (α) stereochemistry which opposes that of cocaine and its active analogs. In fact, when the 3-position-aryl ether system of benztropine is in the α or axial stereochemistry, higher affinity binding results as compared to its β-conformer. In contrast, high affinity binding of cocaine and the WIN series of cocaine analogs is only achieved when the 3-aryl system is in the β- or equatorial conformation. Fourth, substitution in the para-position of one or both phenyl rings significantly affected binding affinity at the dopamine transporter. In contrast, generally, para-substitution in the phenyl ring of either the cocaine or WIN-series of analogs does not change binding affinity as dramatically. Finally, these compounds displace [$^3$H]WIN 35,428 binding monophasically as opposed to the biphasic displacement seen with cocaine, suggesting that these compounds bind to only one site, whereas cocaine recognizes more than one binding domain on the dopamine transporter.

Based on their neurochemical and behavioral properties, the benztropine analogs of the present invention are useful as therapeutics, i.e., cocaine antagonists or cocaine substitutes, for the treatment of cocaine abuse. As such, in another aspect, the present invention provides a method of treating cocaine abuse in a human, the method comprising administering to the human a therapeutically effective amount of a compound having the formula

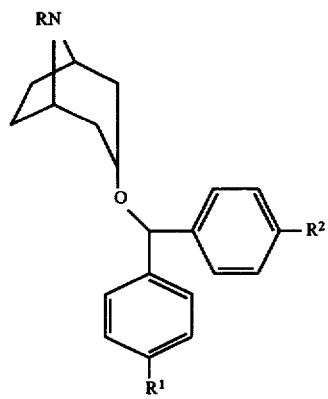

in which: R is a functional group including, but not limited to, hydrogen, alkyl, alkoxy, arylalkyl, aryloxyalkyl, cinnamyl and acyl; and R$^1$ and R$^2$ are independently selected and are functional groups including, but not limited to, hydrogen, alkyl, alkoxy, hydroxy, halogen, cyano, amino and nitro.

Moreover, based on their neurochemical and behavioral properties, the benztropine analogs of the present invention are useful as imaging probes for dopamine transporter/cocaine binding sites and as imaging probes for neurodegenerative disorders (e.g., Parkinson's disease). As such, in another aspect, the present invention provides a method of selectively imaging cocaine binding sites of the central nervous system of a human patient, the method comprising: (a) administering to the central nervous system of the human a compound having the formula

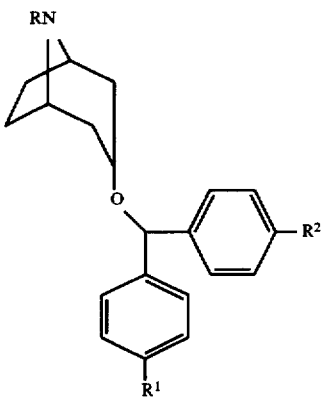

in which: R is a functional group including, but not limited to, hydrogen, alkyl, alkoxy, arylalkyl, aryloxyalkyl, cinnamyl and acyl; and R$^1$ and R$^2$ are independently selected and are functional groups including, but not limited to, hydrogen, alkyl, alkoxy, hydroxy, halogen, cyano, amino and nitro; and (b) detecting the binding of that compound to the central nervous system tissue.

Moreover, in yet another aspect, the present invention provides a method of detecting or monitoring parkinsonism in a human, the method comprising: (a) administering to the human a detectably labeled compound having the formula

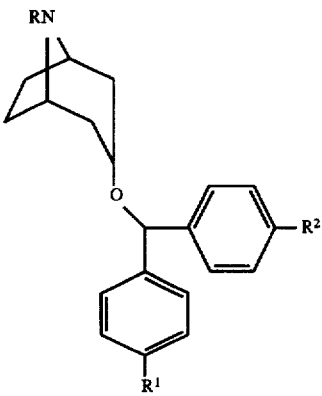

in which: R is a functional group including, but not limited to, hydrogen, alkyl, alkoxy, arylalkyl, aryloxyalkyl, cinnamyl and acyl; and R$^1$ and R$^2$ are independently selected and are functional groups including, but not limited to, hydrogen, alkyl, alkoxy, hydroxy, halogen, cyano, amino and nitro; and (b) detecting the binding of that compound to the central nervous system tissue. Using this method, one can diagnose and/or monitor Parkinson's disease, a neurological disorder characterized by the progressive degeneration of dopamine nerve terminals.

Other features, objects and advantages of the invention and its preferred embodiments will become apparent from the detailed description which follows.

DETAILED DESCRIPTION OF THE INVENTION AND PREFERRED EMBODIMENTS

Figure 1:
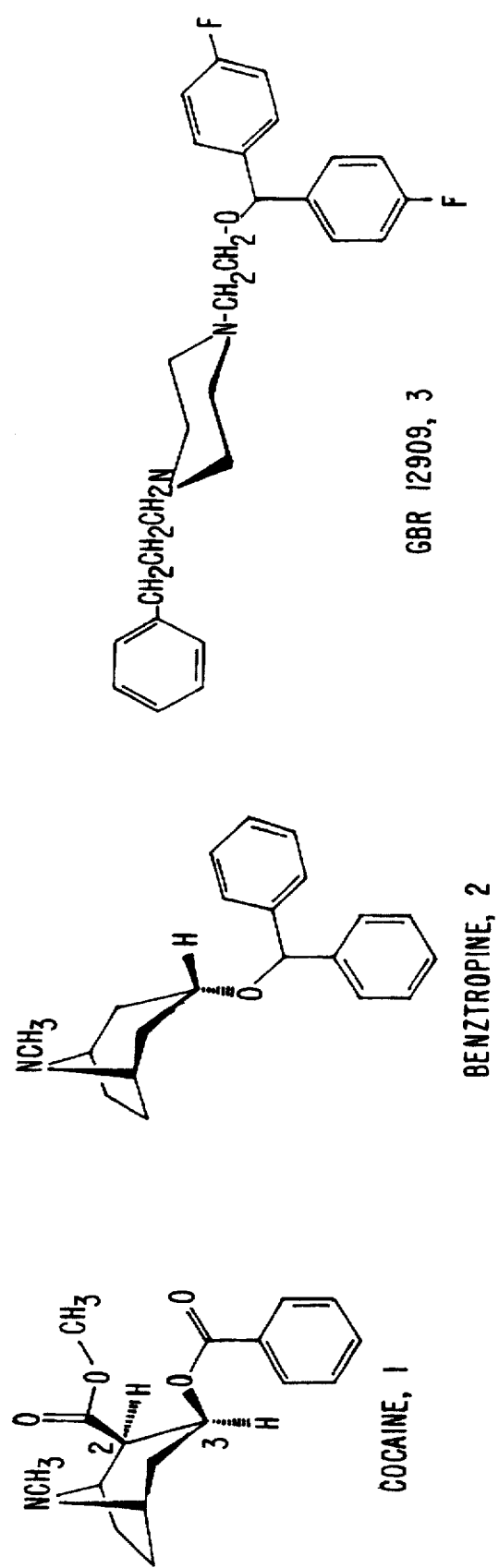
FIG. 1 illustrates the chemical structures of cocaine (1), benztropine (2) and GBR 12909 (3).

In one aspect, the present invention provides compounds having the general formula:

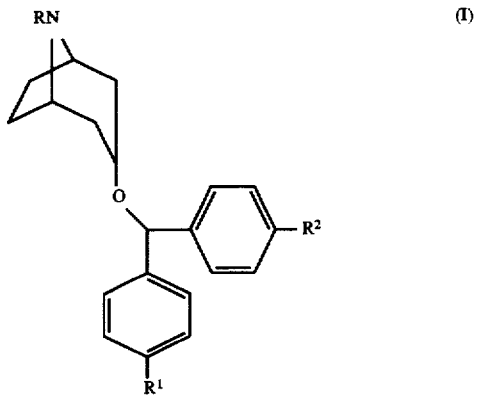

In Formula I, R is a functional group including, but not limited to, hydrogen, alkyl, alkoxy, arylalkyl, aryloxyalkyl, cinnamyl and acyl. In Formula I, $R^1$ and $R^2$ are independently selected and are functional groups including, but not limited to, hydrogen, alkyl, alkoxy, hydroxy, halogen, cyano, amino and nitro.

The term "independently selected" is used herein to indicate that the two R groups, i.e., $R^1$ and $R^2$, can be identical or different (e.g., $R^1$ and $R^2$ may both be methoxy).

The term "alkyl" is used herein to refer a branched or unbranched, saturated or unsaturated, monovalent hydrocarbon radical having from 1–8 carbons, cycloalkyls (3–7 carbons), cycloalkylmethyls (3–8 carbons) and arylalkyls. Suitable alkyl radicals include, for example, methyl, ethyl, n-propyl, i-propyl, 2-propenyl (or allyl), n-butyl, t-butyl, i-butyl (or 2-methylpropyl), cyclopropylmethyl, i-amyl, n-amyl, hexyl, etc. As used herein, the term alkyl encompasses "substituted alkyls." The term "substituted alkyl" refers to alkyl as just described including one or more functional groups such as lower alkyl, aryl, aralkyl, acyl, halogen (i.e., alkylhalos, e.g., $CF_3$), hydroxyl, amino, acylamino, acyloxy, alkoxyl, mercapto and the like. These groups may be attached to any carbon atom of the lower alkyl moiety.

The term "alkoxy" is used herein to refer to the —OR group, where R is a lower alkyl, substituted lower alkyl, aryl, substituted aryl, aralkyl or substituted aralkyl. Suitable alkoxy radicals include, for example, methoxy, ethoxy, phenoxy, t-butoxy, etc.

The term "aryl" refers to an aromatic substituent which may be a single ring or multiple rings which are fused together, linked covalently, or linked to a common group such as an ethylene or methylene moiety. The aromatic ring(s) may include phenyl, naphthyl, biphenyl, diphenylmethyl, 2,2-diphenyl-1-ethyl, and may contain a heteroatom, such as thienyl, pyridyl and quinoxalyl. The aryl group may also be substituted with halogen atoms, or other groups such as nitro, carboxyl, alkoxy, phenoxy, and the like. Additionally, the aryl group may be attached to other moieties at any position on the aryl radical which would otherwise be occupied by a hydrogen atom (such as 2-pyridyl, 3-pyridyl and 4-pyridyl). As such, the terms "arylalkyl" and "aryloxyalkyl" refer to an aryl radical attached directly to an alkyl group (e.g., 3(2-pyridyl) propyl)) or an oxygen which is attached to an alkyl group, respectively.

The term "cinnamyl" is used herein to refer to the 3-phenyl-2-propenyl radical (i.e., Ph.CH:CH.CH$_2$—). The phenyl group may be substituted with halogen atoms or other groups (e.g., nitro, hydroxy, amino, etc.).

The term "acyl" is used herein to refer to the group —C(O)R, where R is hydrogen, alkyl or substituted alkyl, aryl, or substituted aryl as defined above.

The term "cyano" is used herein to refer to the group —CN.

The term "halogen" is used herein to refer to fluorine, bromine, chlorine, and iodine atoms.

The term "hydroxyl" is used herein to refer to the group —OH.

The term "nitro" is used herein to refer to the —NO$_2$ group.

The term "amino" is used herein to refer to the group NRR', where R and R' may independently be hydrogen, lower alkyl, substituted lower alkyl, aryl, substituted aryl or acyl.

Within the scope of Formula I, certain embodiments are preferred, namely those in which R is methyl; R$^1$ is methoxy; and R$^2$ is selected from the group consisting of H and methoxy. Also preferred are compounds in which R is methyl; R$^1$ is nitro; and R$^2$ is H. Also preferred are compounds in which R is methyl; R$^1$ is cyano; and R$^2$ is H. Also preferred are compounds in which R is methyl; R$^1$ is Br; and R$^2$ is selected from the group consisting of H, Br, Cl and F. Also preferred are compounds in which R is methyl; R$^1$ is F; and R$^2$ is selected from the group consisting of H, Br and Cl. Also preferred are compounds in which R is methyl; R$^1$ is an alkyl selected from the group consisting of methyl, ethyl, propyl, butyl, i-butyl, t-butyl, pentyl and hexyl; and R$^2$ is selected from the group consisting of H and alkyl. Also preferred are compounds in which R is methyl; R$^1$ is hydroxy; and R$^2$ is H, hydroxy; Br, Cl and F. Also preferred are compounds in which R is alkyl; and R$^1$ and R$^2$ are independently selected from the group consisting of Br, Cl, F and I. Also preferred are compounds in which R is N-cinnamyl; and R$^1$ and R$^2$ are independently selected from the group consisting of Br, Cl, F and I. Also preferred are compounds in which R is arylalkyl; and R$^1$ and R$^2$ are independently selected from the group consisting of Br, Cl, F and I. It should be noted, however, that if R is methyl, R$^1$ and R$^2$ are selected such that they are not both Cl or F. In addition, if R is methyl and R$^1$ is Cl, R$^2$ is selected, such that it is not hydrogen.

Figure 2:
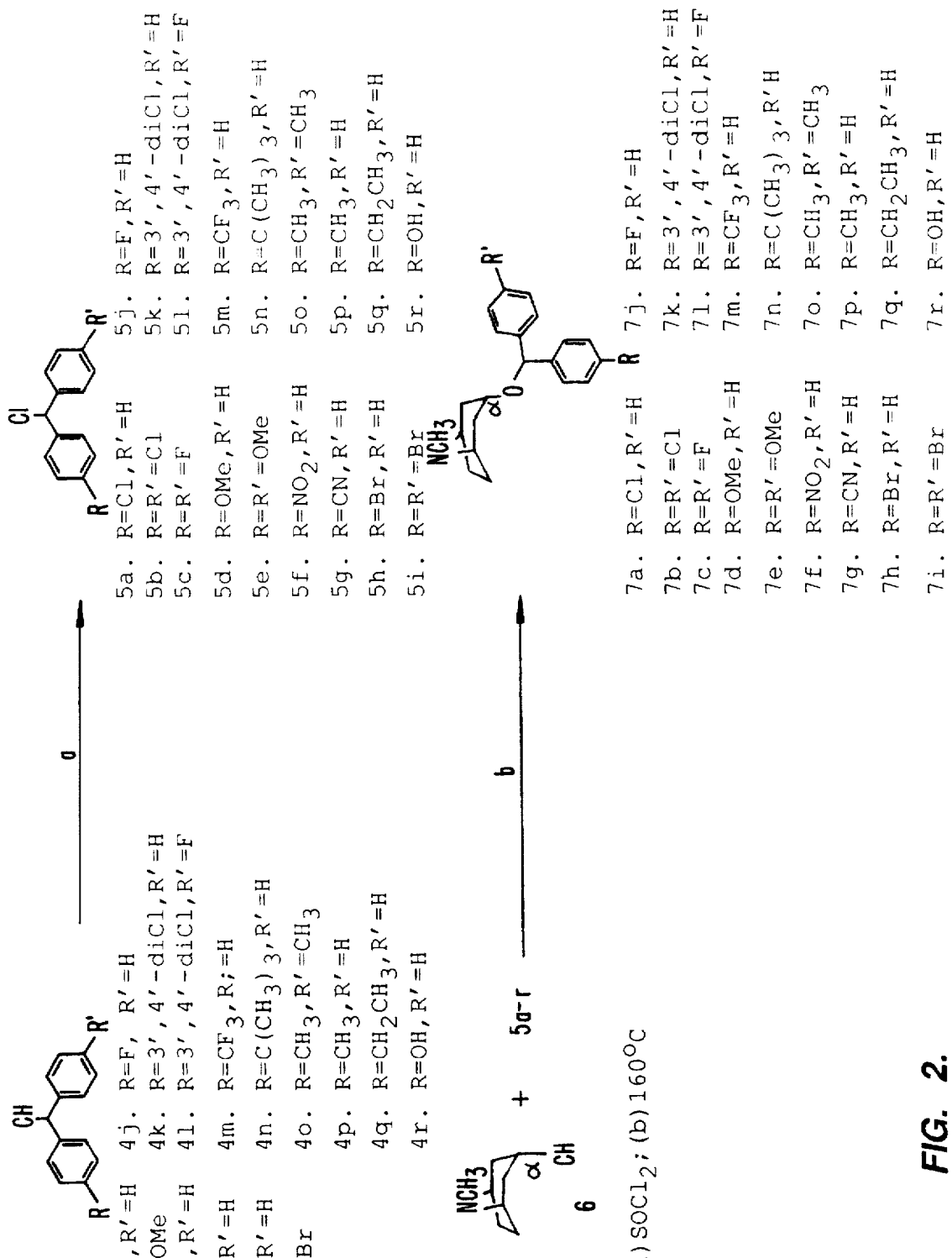
FIG. 2 illustrates the synthetic scheme used to prepare the 4',4"-3α-(diphenylmethoxy)tropane analogs of the present invention.

The compounds of Formula I can be prepared using the synthetic scheme set forth in FIG. 2. Briefly, the 4'- or 4',4"-substituted benzhydrols are converted to the benzhydrylchlorides in refluxing thionyl chloride. The benzhydrylchlorides are then added, neat or in a minimal volume of anhydrous diethyl ether, to tropine at 160° C. to form the 4' or 4',4"-substituted-3α-(diphenylmethoxy)tropane analogs of the present invention. It has been discovered that this second step, i.e., the melt reaction, can be carried out rapidly and without the use or, alternatively, with the minimal use of solvent.

As such, in another aspect, the present invention provides a method for preparing a compound having the formula

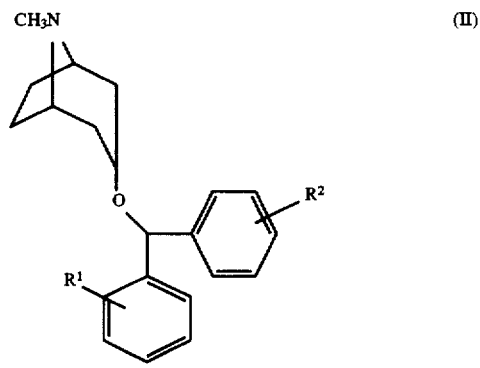

(II)

in which R$^1$ and R$^2$ are independently selected and are functional groups including, but not limited to, hydrogen, alkyl, alkoxy, hydroxy, halogen, cyano, amino and nitro, the method comprising: (a) providing a benzhydrylhalide having the formula

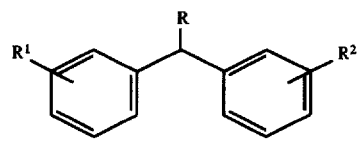

in which R is a halogen selected from the group consisting of Br, Cl, F and I; R$^1$ and R$^2$ are independently selected and are functional groups including, but not limited to, hydrogen, allyl, alkoxy, hydroxy, halogen, cyano, amino and nitro; (b) adding the benzhydrylhalide to a tropine at a temperature of about 140° C. to about 180° C. to form a reaction mixture; and (c) recovering the compound of Formula II from the reaction mixture.

Figure 3:
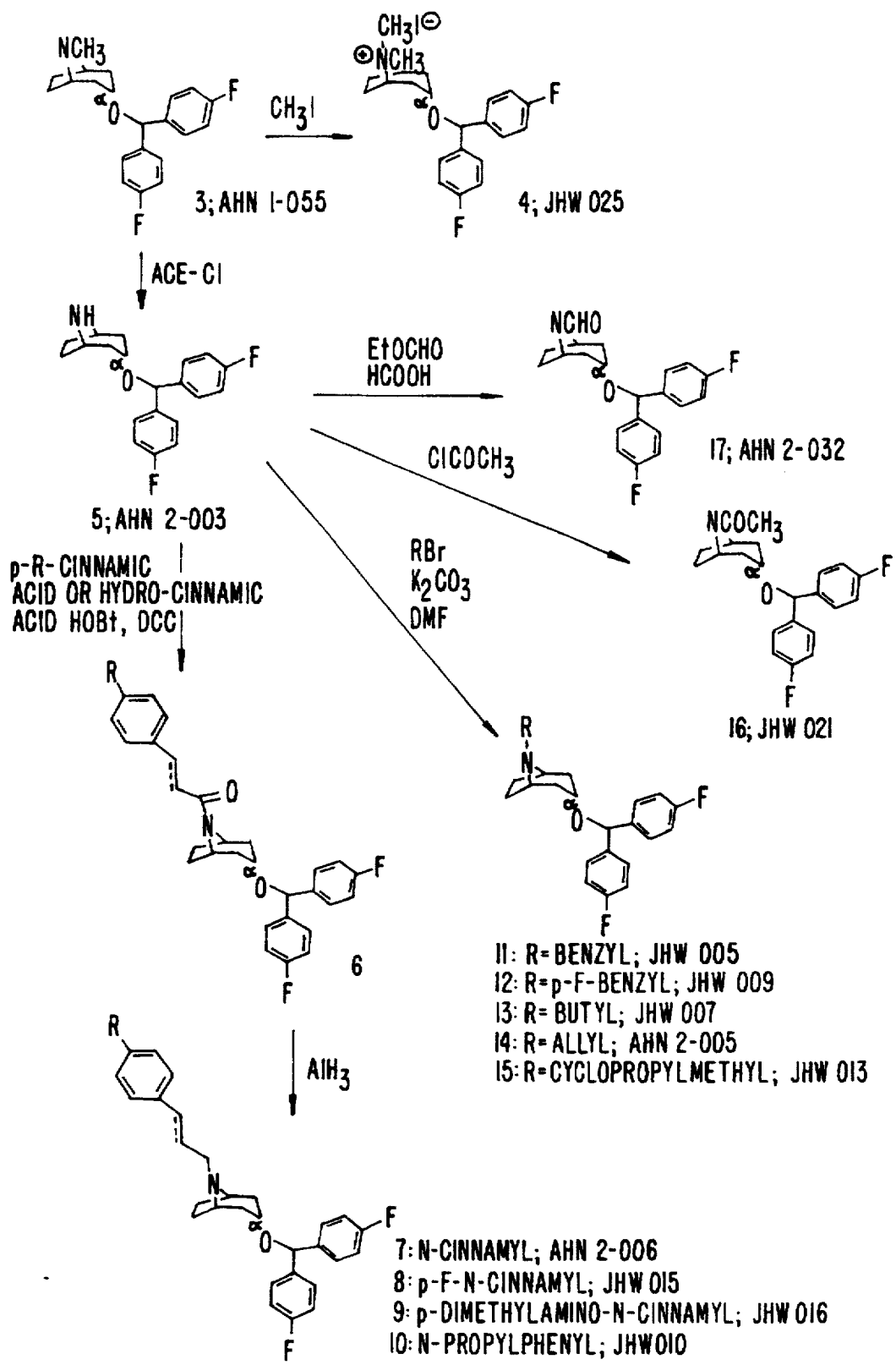
FIG. 3 illustrates the synthetic scheme used to prepare the N-substituted-4',4"-3α-(diphenylmethoxy)tropane analogs of the present invention.

In a presently preferred embodiment, the compound of Formula II is recovered by extraction with aqueous HCl (e.g., 2.8N HCl) to remove residual tropine, followed by washing the aqueous fraction with, for example, CHCl$_3$. Thereafter, the combined organic fractions are evaporated to an off-white foam which can be recrystallized to give the pure product as the HCl salt. It will be readily apparent to those of skill in the art that the N-methyl group on the tropine can be substituted with other functional groups using standard chemical reactions known to and used by those of skill in the art. For example, using the reactions set forth in FIG. 3, the N-methyl group can be replaced with other functional groups including, but not limited to, hydrogen, alkyl, alkoxy, arylalkyl, aryloxyalkyl, cinnamyl and acyl.

Physical properties of exemplary compounds 7a–7e and 10 are set forth in Table I, infra. Physical properties of exemplary compounds 7f–7r are set forth in Table II, infra.

TABLE I

Physical Properties of Compounds 7a–e and 10

| Cmpd no. | rec solv | mp, °C. | MS | formula | % yield |
|---|---|---|---|---|---|
| 7a | 2-PrOH | 212–214 | M+341 | C$_{21}$H$_{25}$NOCl$_2$ | 74 |
| 7b | acetone | 217–219 | M+375 | C$_{21}$H$_{24}$NOCl$_3$ | 70 |
| 7c | acetone | 198–199 | M+343 | C$_{21}$H$_{24}$NOF$_2$Cl-0.75H$_2$O | 83 |
| 7d | EtOAc | 115–117 | M+337 | C$_{22}$H$_{28}$NO$_2$Cl-0.5H$_2$O | 63 |
| 7e | acetone | 180–181 | M+367 | C$_{23}$H$_{30}$NO$_3$Cl | 64 |
| 10 | acetone | 124–126 | M+341 | C$_{21}$H$_{25}$NOCl$_2$-0.25H$_2$O | 31 |

TABLE II

Physical Properties of Compounds 7f–7r.

| Cmpd # | rec. solv. | mp °C. | MS m/z | formula | % yield |
|---|---|---|---|---|---|
| 7f | acetone | 145–151 | M+352 | $C_{21}H_{25}N_2O_3Cl \cdot 0.75H_2O$ | 21 |
| 7g | 2-PrOH | 106–108 | M+332 | $C_{22}H_{25}N_2OCl \cdot 0.75H_2O$ | 40 |
| 7h | acetone | 210–211 | M+386 M+2 388 | $C_{21}H_{25}NOBrCl$ | 70 |
| 7i | acetone | 199–200 | NA* | $C_{21}H_{24}NOBr_2Cl$ | 65 |
| 7j | acetone | 175 | M+325 | $C_{21}H_{25}NOFCl \cdot 0.25H_2O$ | 62 |
| 7k | 2-PrOH/eth | 219–221 | M+375 | $C_{21}H_{24}NOCl_3$ | 58 |
| 7l | EtOAc | 205–206 | M+393 | $C_{21}H_{23}NOCl_3F$ | 63 |
| 7m | EtOAc | 180–182 | M+375 | $C_{22}H_{25}NOF_3Cl \cdot 0.5H_2O$ | 50 |
| 7n | acetone | 243–245 | M+363 | $C_{25}H_{34}NOCl$ | 52 |
| 7o | acetone | 220–222 | M+335 | $C_{23}H_{30}NOCl$ | 63 |
| 7p | EtOAc | 197–199 | M+321 | $C_{22}H_{28}NOCl$ | 60 |
| 7q | EtOAc | 150–153 | M+335 | $C_{23}H_{30}NOCl$ | 45 |
| 7r | MeOH | 240–241 | NA* | $C_{21}H_{26}NO_2Cl$ | 38 |

*Molecular ion peak not observable.

In order to understand the neurochemical and behavioral properties of the compounds of the present invention, exemplary benztropine analogs were evaluated for (1) displacement of [$^3$H]WIN 35,428 (2β-carbomethoxy-3β-(4-fluorophenyl)tropane) binding in rat caudate-putamen, (2) inhibition of [$^3$H]dopamine uptake in rat caudate-putamen, (3) stimulation of ambulatory activity in mice which is a characteristic effect of psychomotor stimulant drugs (see, Kelleher, R. T., Psychomotor Stimulants. In *Drug Abuse: The Clinical and Basic Aspects;* Pradhan, S. N., Dutta, S. M., Eds; Mosby St. Louis, Mo., 1977), and (4) substitution for cocaine in rats trained to discriminate 10 mg/kg of cocaine from saline (see, Witkin, J. M., et al., *J. Pharmacol. Exp. Ther.* 1991, 257, 706–713). In carrying out the foregoing assays, it has been determined that the compounds of the present invention have the following properties: they have a high affinity for the dopamine transporter; they inhibit dopamine uptake; and, quite surprisingly, they do not exhibit a cocaine-like behavioral profile.

More particularly, 4'-and 4',4"-substituted-3α-(diphenylmethoxy)tropane analogs (7a–7r and 10) were evaluated for displacement of radiolabeled ligand binding at the dopamine (DAT), serotonin (5HTT) and norepinephrine (NET) transporters as well as muscarinic $m_1$ and $m_2$ receptors, Table III, infra. In addition, several exemplary N-substituted-4',4"-3α-(diphenylmethoxy)tropane analogs were evaluated for displacement of radiolabeled ligand binding at the dopamine (DAT), serotonin (5HTT) and norepinephrine (NET) transporters as well as muscarinic $m_1$ and $m_2$ receptors, Table III, infra. All of the compounds tested monophasically displaced [$^3$H]WIN 35,428 binding at the dopamine transporter with a wide range of affinities ($K_i$=11.8 to 2000 nM). The most potent compound in this exemplary series is the 4',4"-difluoro analog (7c), $K_i$=11.8 nM. All of the 4'- and 4',4"-halogen-substituted compounds bound with higher affinity at the dopamine transporter than the unsubstituted parent compound, benztropine, with F>Cl>Br.

In general, it was found that increasing steric bulk on one and especially on both phenyl rings significantly decreased binding affinity at the dopamine transporter, i.e., 7n ($K_i$= 1918 nM) and 7e ($K_i$=2000 nM) vs. 7d ($K_i$=78.4 nM). Further, both electronic and lipophilic properties of these substituents appear to be playing a role since the halogenated compounds were more potent than the parent drug, and the compounds with more strongly electron-withdrawing substituents such as 4'-$CF_3$-substituent in 7m ($K_i$=635 nM) were less potent than the comparably sized 4'-$CH_3$-substituted analog, 7p ($K_i$=187 nM). Moreover, in the benztropine series, the 3α-diphenyl ether was favored over the 3β-configuration, i.e., 7a ($K_i$=30 nM) vs. 10 ($K_i$= 854 nM). Quite surprisingly, this configuration, i.e., α or axial aryl, is opposite to the favored β- or equatorial configuration of the aryl substituents for the cocaine and WIN analogs (Carroll, F. I., et al., *J. Med. Chem.* 1992, 35, 969–981).

None of the 4'- or 4',4"-substituted-3α-(diphenylmethoxy)tropane analogs bound with high affinity to either norepinephrine or serotonin transporters. At the norepinephrine transporter, none of the compounds displaced >60% of [$^3$H]desmethylimipramine binding at a concentration of 10 μM. For example, compound 7c was >700-fold more potent at the dopamine transporter as compared to the norepinephrine transporter. Further, this compound is >200-fold selective for the dopamine vs. the serotonin transporter. Hence, the 4' or 4'4"-substituted-3α-(diphenylmethoxy)tropane analogs of the present invention are some of the most selective compounds for the dopamine transporter over the other monoamine transporters reported to date.

TABLE III

Results of Radiolabeled Binding Experiments on 4'- and 4',4"-substituted-3-α-(diphenylmethoxy)tropane analogs.

| Compound # | Substitution | DAT $K_i$, nM (% error)$^a$ | NET$^{b,c}$ (% I@10 μM) | 5HTT$^{b,c}$ (% I@10 μM) | $m_1$, Ki, nM$^c$ | $m_2$, $K_i$, nM$^c$ |
|---|---|---|---|---|---|---|
| 7c | 4',4"-diF | 11.8 (11)$^e$ | 30[>8500]$^d$ | 62[>2440]$^d$ | 6.1 | 48.8 |
| 7l | 3',4'-diCl,4"-F | 18.9 (14) | 57.8[>9000]$^d$ | 80.3[>691]$^d$ | 33 | 369 |

TABLE III-continued

Results of Radiolabeled Binding Experiments on 4'- and 4',4"-substituted-3-α-(diphenylmethoxy)tropane analogs.

| Compound # | Substitution | DAT $K_i$, nM (% error)[a] | NET[b,c] (% I@10 μM) | 5HTT[b,c] (% I@10 μM) | $m_1$, Ki, nM[c] | $m_2$, $K_i$, nM[c] |
|---|---|---|---|---|---|---|
| 7b | 4',4"-diCl | 20.0 (14)[e] | 43[>6000][d] | 54[>2960][d] | 35 | 1490 |
| 7k | 3'4'-diCl | 22.1 (19) | 56.5[>4870][d] | 66.2[>1790][d] | 12.5 | 141 |
| 7a | 4'-Cl | 30.0 (12)[e] | 32 | 34 | 3.6 | 36.6 |
| 7j | 4'-F | 32.2 (10) | 37.9 | 35.2 | 1.1 | 15.0 |
| 7h | 4'-Br | 37.9 (7) | 37 | 39 | 3.7 | 39.1 |
| 7d | 4'-OMe | 78.4 (8)[e] | 30.9 | 30.5 | 4.2 | 18.9 |
| 7i | 4'-4"-diBr | 91.6 (13) | 41.1 | 41 | 70.8 | 66%[b] |
| 2 | — | 118 (9)[e] | 18.3 | 17.2 | 0.95 | 2.6 |
| 7p | 4'-CH$_3$ | 187 (5) | 31.8 | 35.4 | 2.7 | 37.5 |
| 7g | 4'-CN | 196 (9) | 16 | 40 | 7.1 | 74.0 |
| 7f | 4'-NO$_2$ | 197 (8) | 29 | 54[>3570][d] | 7.1 | 41.9 |
| 7r | 4-OH | 297 (13) | 27.3 | 23.3 | 2.1 | 17.7 |
| 7o | 4',4"-diCH$_3$ | 420 (7) | 35.1 | 35.5 | 47.2 | 716 |
| 7q | 4'-CH$_2$CH$_3$ | 520 (8) | 32.7 | 42.7 | 12.6 | 703 |
| 7m | 4'CF$_3$ | 635 (10) | 34.6 | 49.1 | 5.4 | 1510 |
| 10 | 3β-4'-Cl | 854 (7)[e] | 27.9 | 37.2 | 4.1 | 87.4 |
| 7n | 4'C(CH$_3$)$_3$ | 1918 (7) | 37.6 | 24.7 | 148 | 54%[b] |
| 7e | 4',4"-diOMe | 2000 (7)[e] | 34 | 31 | 39.6 | 1000 |
| cocaine | — | 32 (16)/388 (57)[f] | — | — | | |
| GBR 12909 | — | 11.6 (31)[f] | — | — | | |

[a]Each $K_i$ value represents data from at least three independent experiments, each performed in triplicate.
[b]% Inhibition of radiolabeled ligand binding at a concentration of 10 μM,
[c]data provided by NOVASCREEN.
[d]$K_i$ value in nM.
[e]Data from reference 13.
[f]Data from reference 24.

TABLE IV

Results of Radiolabeled Binding and Inhibition of [$^3$H]-Dopamine Uptake Experiments on N-substituted 4',4"-diF-BZT analogs

| compound # | substitution | DAT, $K_i$, nM[a] | [$^3$H]DAU | NET, $K_i$, nM[c] | 5HHT, $K_i$, nM[c] | $m_1$, $K_i$, nM[c] | $m_2$, $K_i$, nM[c] |
|---|---|---|---|---|---|---|---|
| AHN 2-003 | NH | 11.2 (11) | 10 | >8000 | 2100 | 90.7 | 620 |
| AHN 1-055 | N—CH$_3$ | 11.8 (11) | 71 | >8500 | 2440 | 6.1 | 48.8 |
| JHW 007 | N-butyl | 24.6 (8) | 371[d] | 1330 | 1730 | 527 | 308 |
| AHN 2-005 | N-allyl | 29.9 (10) | 14 | 22.1%[b] | 1970 | 89.1 | 254 |
| JHW 013 | N-c-PM | 32.4 (9) | 180 | 117 | 53.4 | 7.7 | NT |
| JHW 010 | N-propyl-Ph | 41.9 (11) | 227 | 3520 | 375 | 273 | 499 |
| JHW 005 | N-Bz | 82.2 (15) | 285 | 2080 | 1810 | 2490 | 276 |
| AHN 2-006 | N-cinnamyl | 86.4 (12) | 184 | 577 | 1490 | 240 | 1590 |
| JKW 009 | N-p-F-Bz | 95.6 (10) | 204 | 60%[b] | 53.4 | 0.45 | NT |
| AHN 2-032 | NCHO | 2021 (13) | 5384 | 29%[b] | 1.6%[b] | 54%[b] | 62%[b] |

[a]Each $K_i$ value represents data from at least three independent experiments, each performed in triplicate.
[b]% Inhibition at 10 μM,
[c]data provided by NOVASCREEN.
[d]biphasic inhibition curve.

In addition, all of the analogs tested bound with high affinity ($K_i$=0.95 to 70.8 nM) to muscarinic $m_1$ receptors. In all cases, substitution at the 4' and/or 4"-position(s) served to decrease affinity at this site, with the 4',4"-dibromo analog (71) having >70-fold lower affinity for these receptors than the parent benztropine. Interestingly, although affinities at $m_1$ and $m_2$ sites were correlated (r=0.954; p<0.0011), some of these compounds were remarkably selective for the $m_1$ over $m_2$ sites, such as compound 7m which was nearly 300-fold more selective for $m_1$ sites.

The parent drug, i.e., benztropine, demonstrated a >100-fold higher affinity for $m_1$ receptors compared to the dopamine transporter. In contrast, the compounds that were most potent at the dopamine transporter, 7c, 71, 7b, and 7k, had similar binding affinities at muscarinic $m_1$ receptors, suggesting that chemical modification that increase binding affinities at the dopamine transporter do not concomitantly increase binding affinities at the muscarinic receptors and, therefore, a separation of these actions appears to be achievable. In fact, affinity at the dopamine transporter was correlated with neither affinity at $m_1$ (r=0.323; p=0.1653) nor $m_2$ (r=0.353; p=0.1267) sites likewise suggesting that dopamine uptake inhibition and antimuscarinic actions will be separable within the 3α-(diphenylmethoxy)tropane series of compounds.

Figure 4:
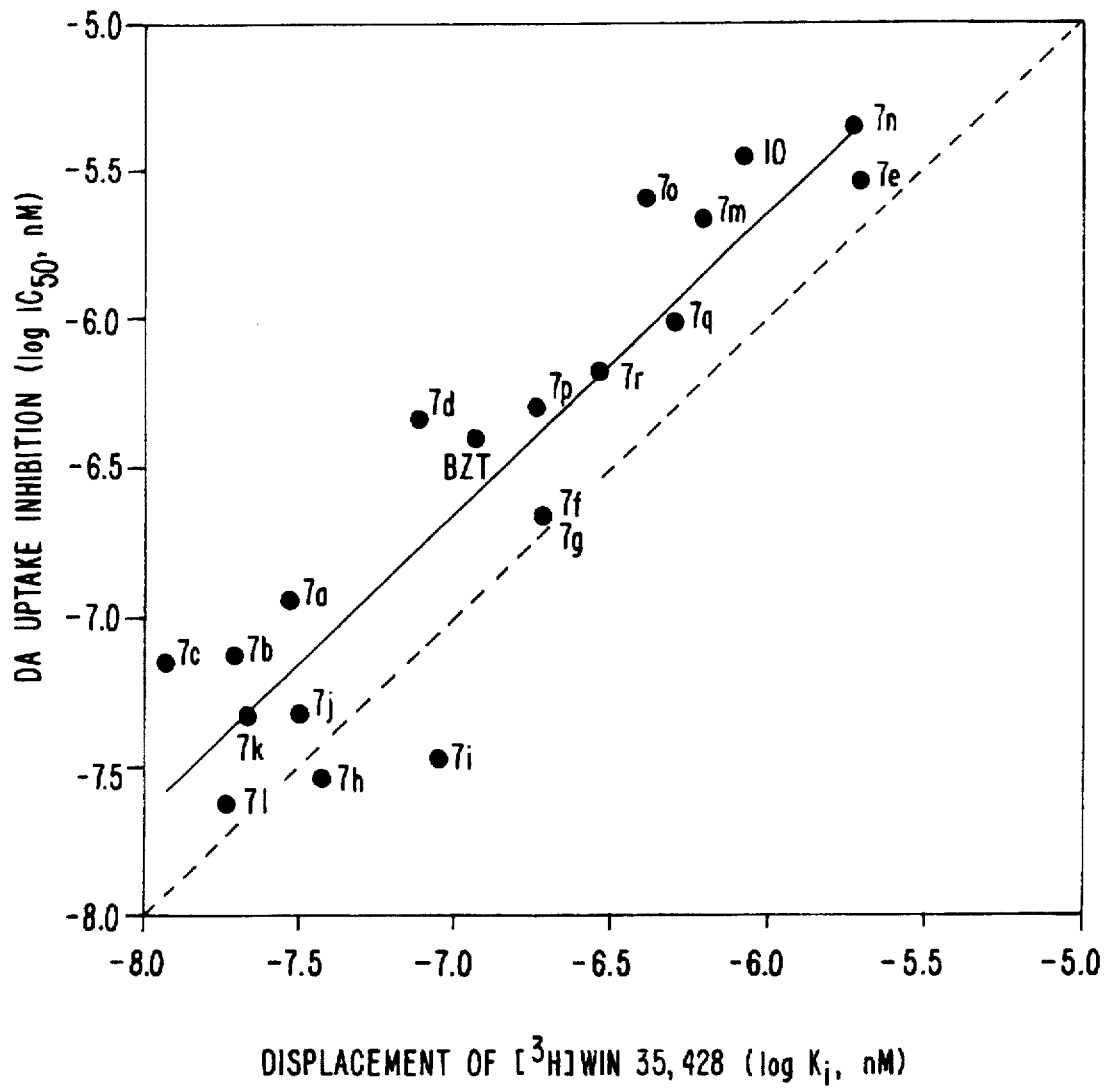
FIG. 4 illustrates the correlation of $K_i$ values for displacement of [$^3$H]WIN 35,428 and $IC_{50}$ values for inhibition of dopamine uptake in tissue from rat caudate putamen.
Figure 5:
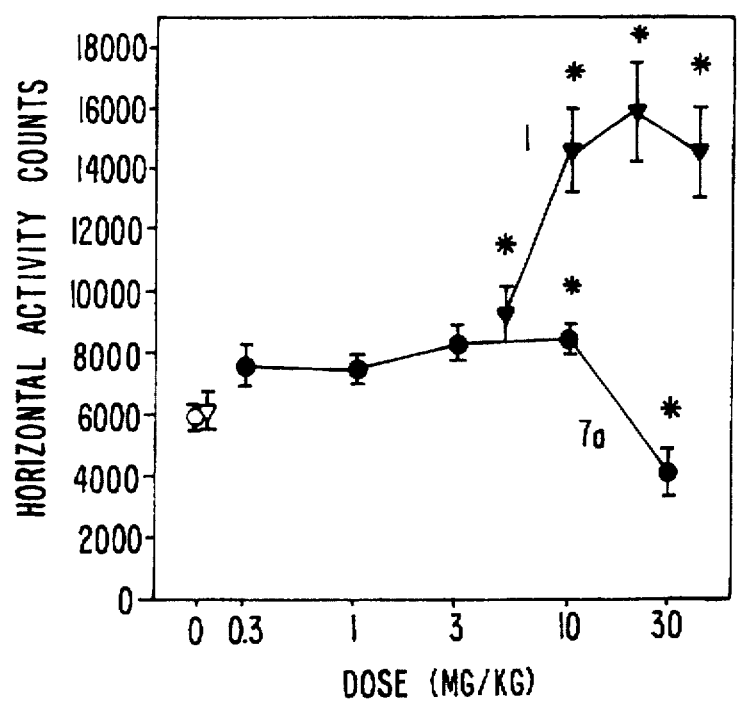
FIG. 5 illustrates the dose-dependent effects of cocaine (1) and 4-chlorobenztropine (7a) on locomotor activity in mice. Ordinates: horizontal activity counts after drug administration. Abscissae: dose of drug in mg/kg, log scale. Unfilled points above C represent the effects of saline vehicle controls. Each point represents the average effect determined in eight mice. The data are from the first 30-min period after drug administration, in which the greatest stimulant effects were obtained. The asterisks represent points that are significantly different from vehicle controls.
Figure 6:
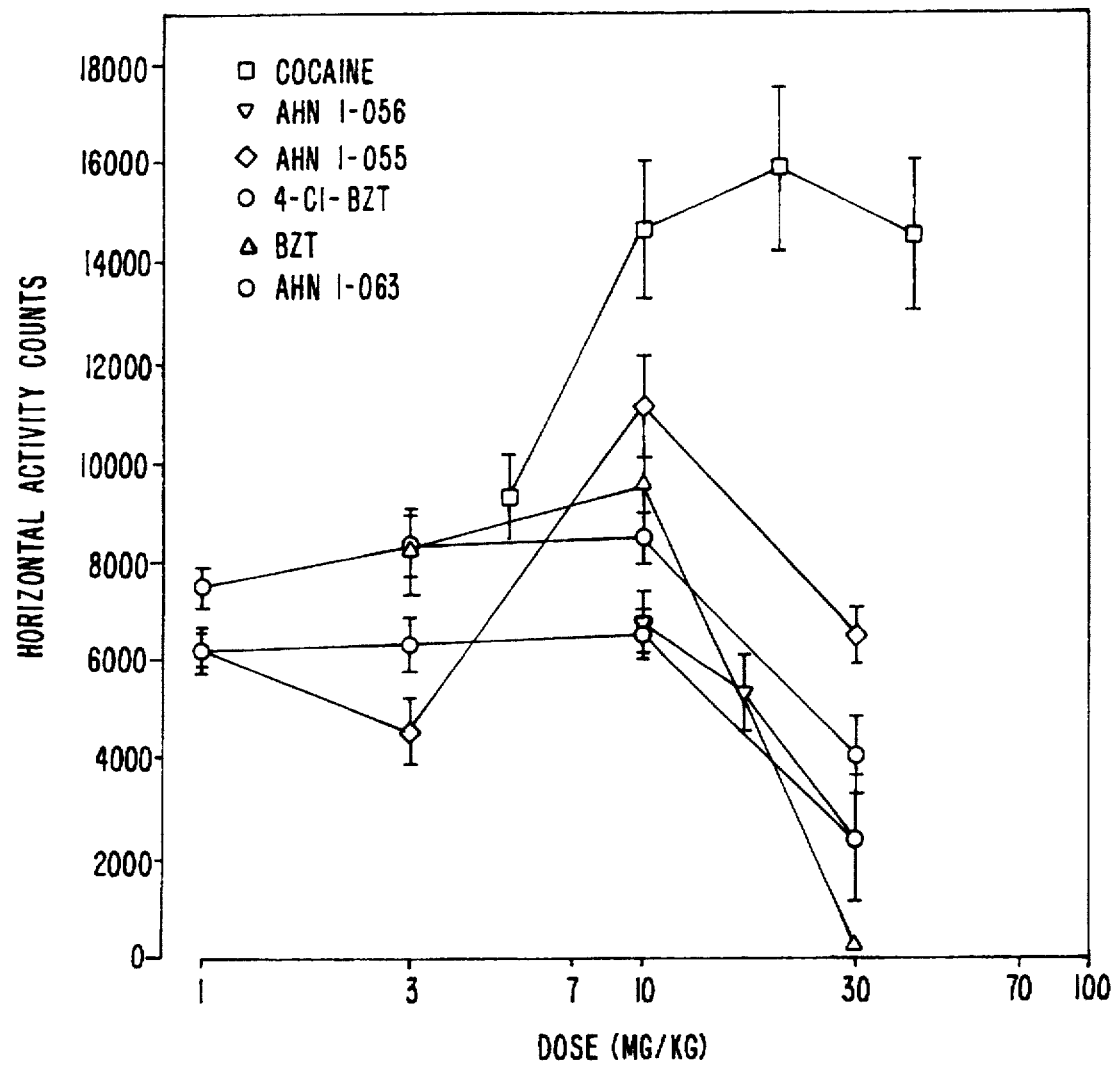
FIG. 6 illustrates the dose-dependent effects of cocaine, 4'-methoxy-3α-(diphenylmethoxy)tropane (AHN 1-056), 4',4"-difluoro-3α-(diphenylmethoxy)tropane (AHN 1-055), 4'-Cl-3α-(diphenylmethoxy)tropane, 3α-(diphenylmethoxy)-1αH,5αH-tropane and 4'-Cl-3β-(diphenylmethoxy)tropane (AHN 1-063) on locomotor activity in mice. Ordinates: horizontal activity counts after drug administration. Abscissae: dose of drug in mg/kg, log scale.
Figure 7:
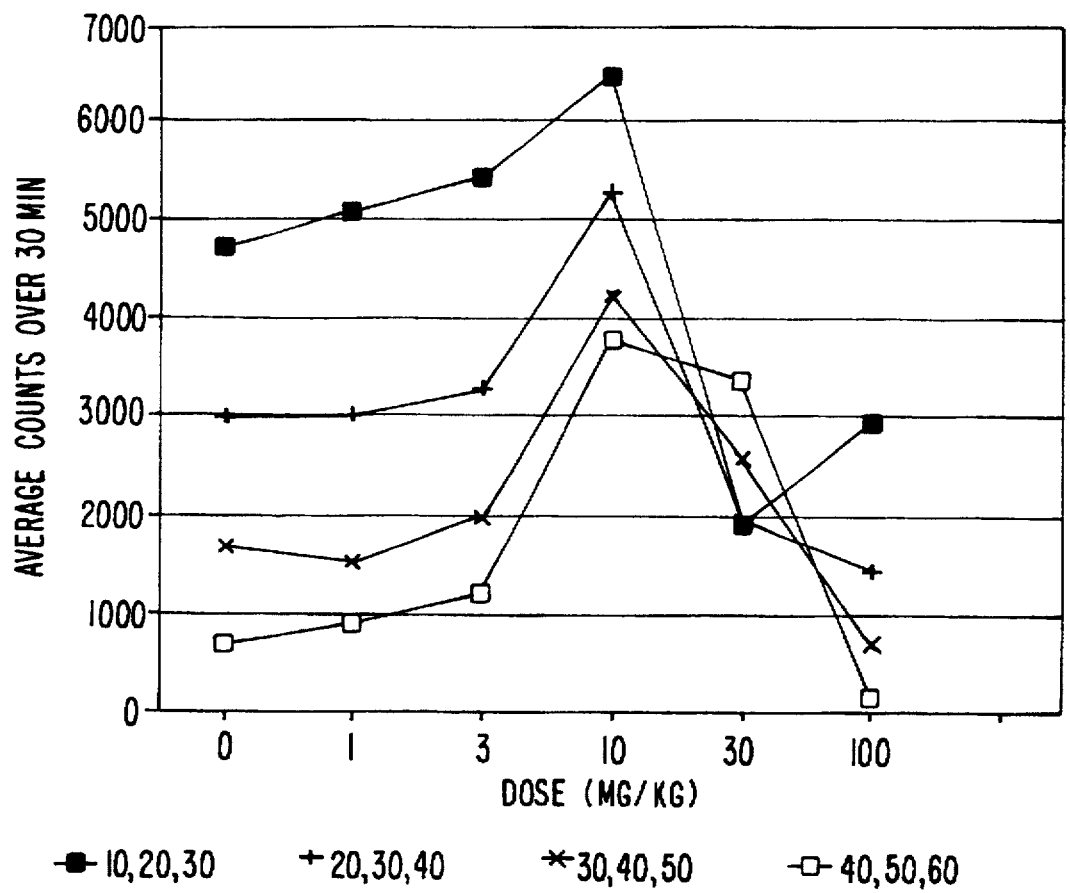
FIG. 7 illustrates the dose-dependent effects of N-allyl-4',4"-difluorobenztropine (AHN 2-005) on locomotor activity in mice starting at various points in time (e.g., starting at 0 minutes, 10 minutes, 20 minutes and 30 minutes after administration of the compound). Ordinates: horizontal activity counts after drug administration. Abscissae: dose of drug in mg/kg, log scale.
Figure 8:
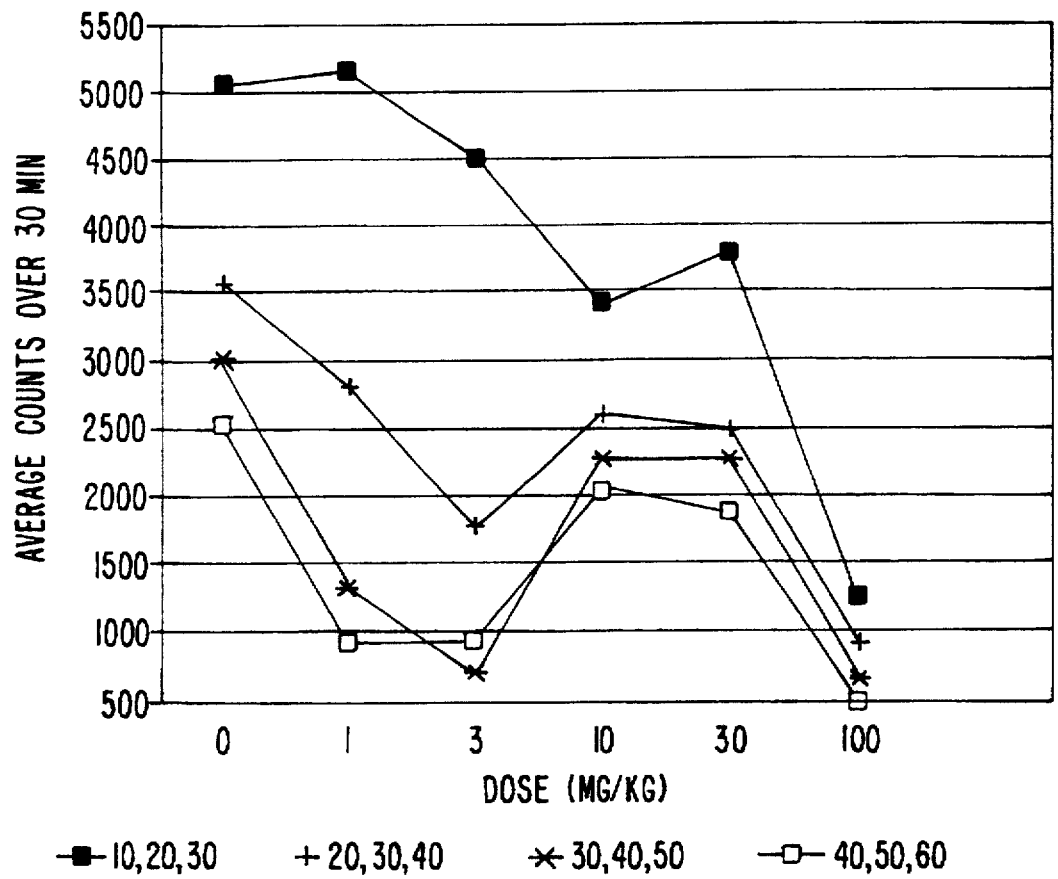
FIG. 8 illustrates the dose-dependent effects of N-nor-4',4"-difluorobenztropine (AHN 2-003) on locomotor activity in mice starting at various points in time (e.g., starting at 0 minutes, 10 minutes, 20 minutes and 30 minutes after administration of the compound). Ordinates: horizontal activity counts after drug administration. Abscissae: dose of drug in mg/kg, log scale.

In addition, exemplary 4'- or 4',4"-substituted 3α-(diphenylmethoxy)tropane analogs, i.e., compounds 7a–7r, were evaluated for inhibition of [$^3$H]dopamine uptake in rat caudate putamen, Table V, infra. In addition, exemplary N-substituted-4'- or 4',4"-substituted 3α-(diphenylmethoxy) tropane analogs were evaluated for inhibition of [$^3$H] dopamine uptake in rat caudate putamen, Table IV, supra. All of the compounds that bound with high affinity to the dopamine transporter were potent inhibitors of dopamine uptake. This was evidenced by the high, significant correlation (r=0.907; p<0.0001) between log $K_i$ values for binding and log $IC_{50}$ values for inhibiting dopamine uptake, FIG. 4.

In the N-substituted-4',4"-difluorobenztropine series (Table IV), all but compound AHN 2-032 bound with high affinity to the dopamine transporter ($K_i$ values=11.2–95.6 nM) and inhibited dopamine uptake with an $IC_{50}$ value of 10–371 nM. Several of these compounds demonstrated significantly lower binding affinities at the muscarinic $m_1$ and $m_2$ receptors as compared to binding affinities at the dopamine transporter (i.e., JHW 005 and JHW 007). Most of these analogs were not potent at either the NET or 5-HHT.

TABLE V

[$^3$H]Dopamine Uptake Inhibition by 4'- and 4',4"-substituted-3-α-(diphenylmethoxy)tropane analogs.[a]

| Compound # | Substitution | [$^3$H]DA Uptake Inhibition $IC_{50}$ (nM) |
|---|---|---|
| 7l | 3',4'-diCl,4"-F | 24 |
| 7h | 4'-Br | 29 |
| 7i | 4',4"-diBr | 34 |
| 7k | 3',4'-diCl | 47 |
| 7j | 4'-F | 48 |
| 7c | 4',4"-diF | 71 |
| 7b | 4',4"-diCl | 75 |
| 7a | 4'-Cl | 115 |
| 7f | 4'-NO$_2$ | 219 |
| 7g | 4'-CN | 222 |
| 2 | — | 403 |
| 7d | 4'-OMe | 468 |
| 7p | 4'-CH$_3$ | 512 |
| 7r | 4'-OH | 677 |
| 7q | 4'-CH$_2$CH$_3$ | 984 |
| 7m | 4'-CF$_3$ | 2155 |
| 7o | 4',4"-diCH$_3$ | 2536 |
| 7e | 4',4"-diOMe | 2876 |
| 10 | 3β-4'-Cl | 3519 |
| 7n | 4'-C(CH$_3$)$_3$ | 4456 |

[a]Each value represents data from at least three independent experiments, each performed in triplicate.

Figure 9A:
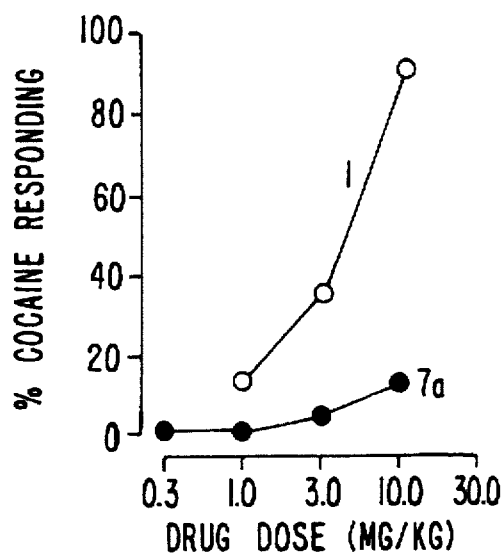
FIGS. 9A and 9B illustrate the effects of cocaine (1) and 4-chlorobenztropine (7a) in rats trained to discriminate injections of cocaine (1) from saline. Ordinates: percentage of responses on the cocaine-appropriate lever. Abscissae: drug dose in mg/kg (log scale). 9A: percentage of responses emitted on the lever on which rats were trained to respond after injections of cocaine (1). 9B: rates at which responses were emitted as a percentage of response rate after saline administration. Each point represents the effect in four or six rats.
Figure 9B:
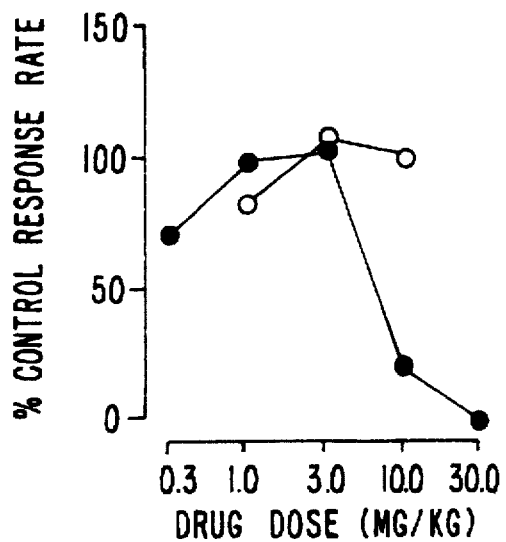
Figure 10A:
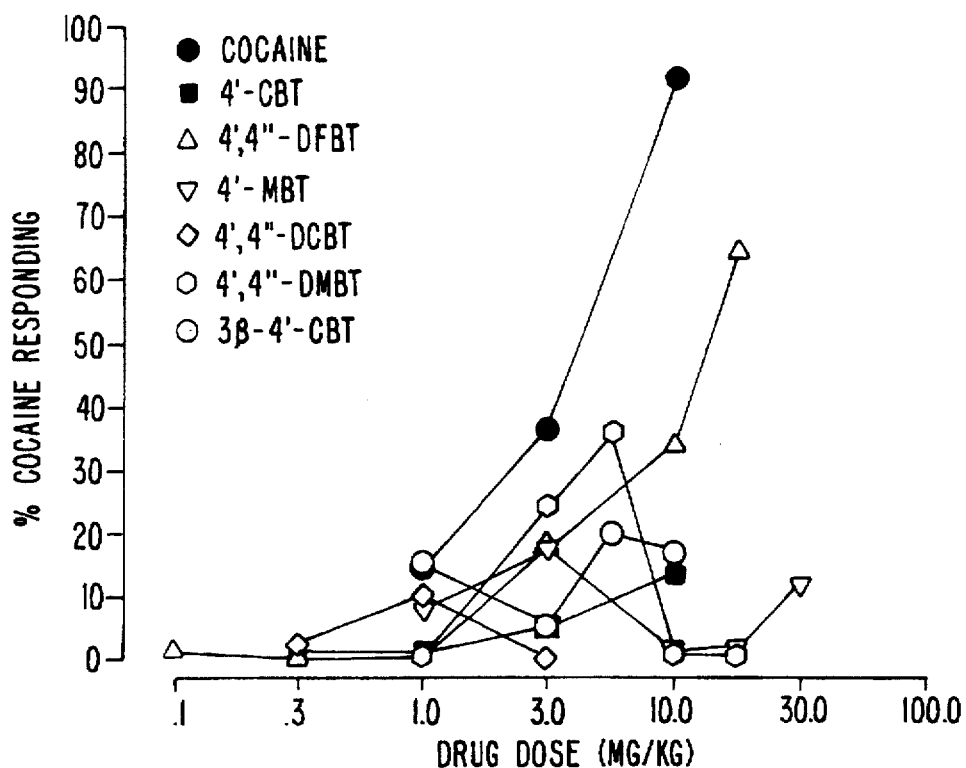
FIGS. 10A and 10B illustrate the effects of various compounds in rats trained to discriminate injections of cocaine (1) from saline. Ordinates: percentage of responses on the cocaine-appropriate lever. Abscissae: drug dose in mg/kg (log scale). 10A: percentage of responses emitted on the lever on which rats were trained to respond after injections of cocaine (1). 10B: rates at which responses were emitted as a percentage of response rate after saline administration. Each point represents the effect in four or six rats.
Figure 10B:
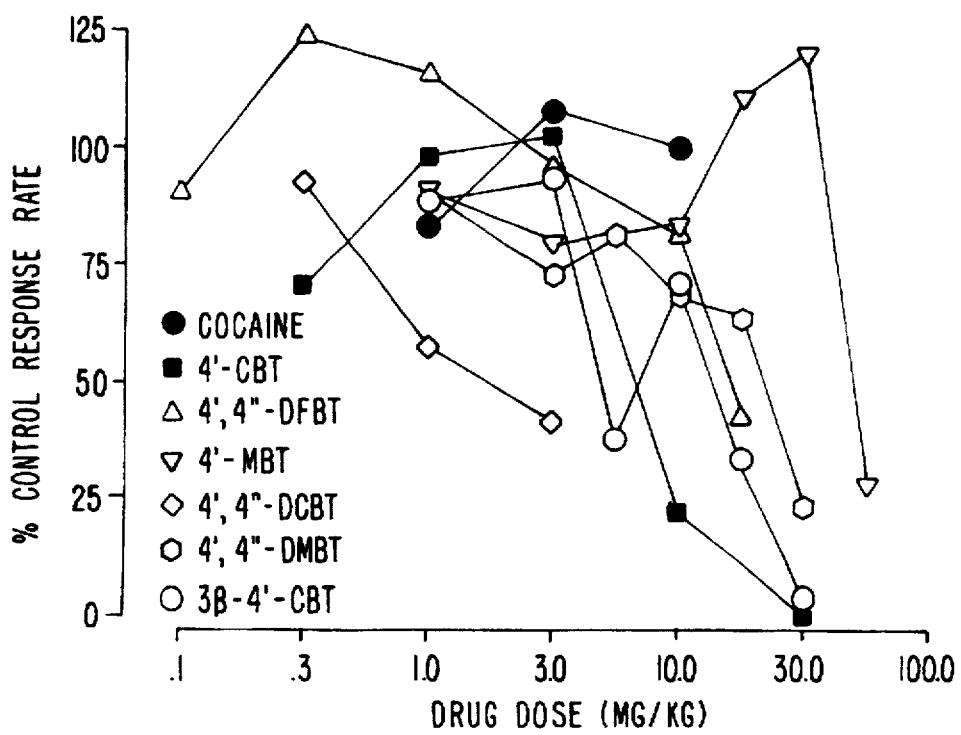
Figure 11A:
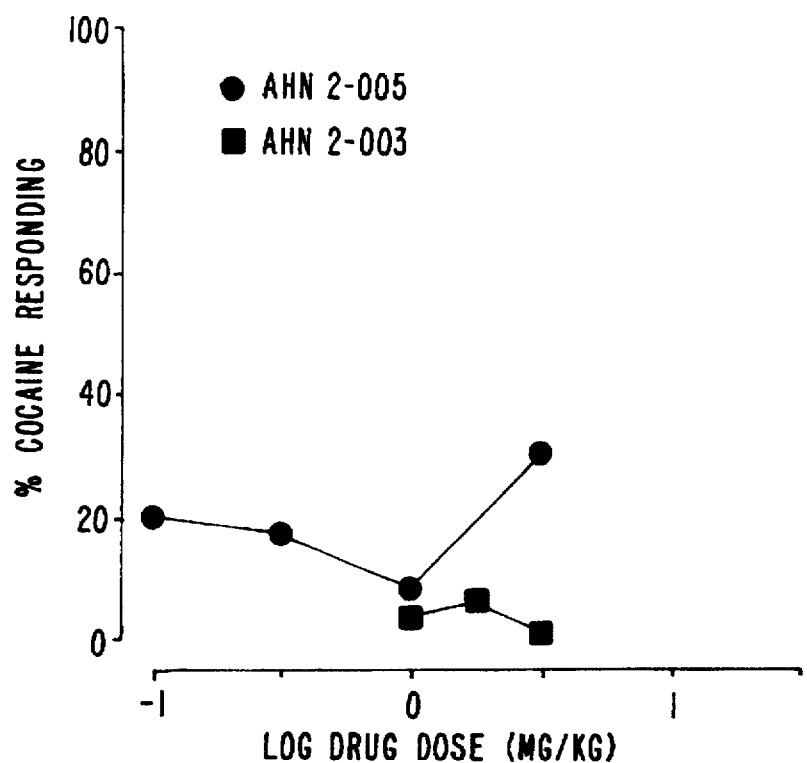
FIGS. 11A and 11B illustrate the effects of N-allyl-4',4"-difluorobenztropine (AHN 2-005) and N-nor-4',4"-difluorobenztropine (AHN 2-003) in rats trained to discriminate injections of cocaine (1) from saline. Ordinates: percentage of responses on the cocaine-appropriate lever. Abscissae: drug dose in mg/kg (log scale). 11A: percentage of responses emitted on the lever on which rats were trained to respond after injections of cocaine (1). 11B: rates at which responses were emitted as a percentage of response rate after saline administration. Each point represents the effect in four or six rats.
Figure 11B:
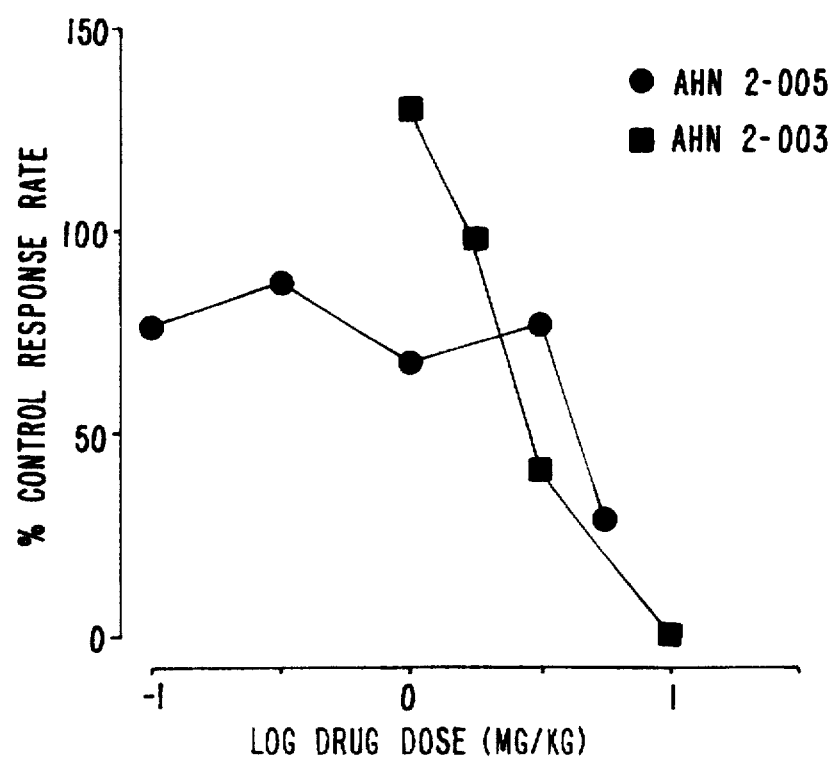

However, in contrast to the cocaine analogs known to date (see, Cline, E. J., et al., *J. Pharmacol. Exp. Ther.* 1992, 260, 1174–1179), behavioral studies on the 4',4"-3α-(diphenylmethoxy)tropane analogs of the present invention, e.g., compounds 7a–7e, reveal that such dopamine uptake inhibitors are not efficacious locomotor stimulants (See, FIGS. 5–8). Further, in contrast to the cocaine analogs known to date (see, e.g., Cline, E., et al., *Behav. Pharmacol.* 1992, 3, 113–116), the dopamine uptake inhibitors of the present invention do not produce a cocaine-like discriminative stimulus as demonstrated by their lack of generalization to the cocaine cue in rats trained to discriminate 10 mg/kg of cocaine from saline (See, FIGS. 9–11). The observation that these tropane analogs are neurochemically similar and yet behaviorally distinct from cocaine is very intriguing and, at this time, the reasons for this dichotomy are unclear. Without being bound by any theory, there are several potential explanations which warrant further investigation. For example, all of the benztropine analogs of the present invention bind with high affinity to muscarinic sites and those actions may interfere with the expression of a cocaine-like psychomotor stimulant effect. In the compounds behaviorally tested to date, there is not a large difference in binding affinities at the muscarinic $m_1$ sites ($K_i$ range= 3.6–39.6), and the separation of binding affinities for the dopamine transporter and muscarinic $m_1$ sites is negligible. Therefore, at this time, the role of the muscarinic antagonist properties of these compounds in their behavioral effects cannot be fully assessed. Compounds that retain high affinity at the dopamine transporter, but have significantly lower affinities for the muscarinic $m_1$ sites are necessary to fully determine whether this receptor system is playing a role in the pharmacology of these compounds.

Alternatively, it has been reported previously that [$^3$H]WIN 35,428 exhibits two binding components on the dopamine transporter (see, e.g., Izenwasser, S., et al., *Eur. J. Pharmacol.* 1994, 263, 277–283; and Madras B. K., et al., *Mol. Pharmacol.* 1989, 36, 518–524). Further, a two-site model for the binding of cocaine and several other dopamine uptake inhibitors is preferred over a one-site model when assays are conducted with either [$^3$H]cocaine or [$^3$H]WIN 35,428. In addition, locomotor activity is well correlated with the binding affinities of the compounds at the high affinity site, whereas no correlation exists between this behavior and binding at the low affinity component (See, Izenwasser, S., et al., supra, 1994). Since benztropine and the benztropine analogs of the present invention monophasically displace [$^3$H]WIN 35,428 and do not produce locomotor stimulant activity, it may be speculated that these compounds are interacting at a low affinity component on the dopamine transporter, which may not be associated with psychomotor stimulant actions. Of course, further characterization of compounds that interact exclusively at one component or the other is necessary before any conclusions can be drawn.

As such, the compounds of the present invention have the following properties: (1) they have a high affinity for the dopamine transporter; (2) they inhibit dopamine uptake; and (3) they do not exhibit a cocaine-like behavioral profile.

Based on their neurochemical and behavioral properties, the benztropine analogs of the present invention are useful as therapeutics for the treatment of cocaine abuse. These compounds inhibit dopamine uptake and, thus, provide elevated levels of extracellular dopamine that alleviate the symptoms of cocaine abstinence (see, Rothman, R. B., et al., *Life Sci. Pharmacol. Lett.* 1990, 46, PL-17-PL-21) in a manner similar to the way in which the nicotine patch or nicotine chewing gum protects against withdrawal symptoms after cessation of tobacco use. Further, as a result of their lack of cocaine-like behavioral effects, these compounds are not subject to abuse themselves. Thus, the benztropine analogs of the present invention can serve to keep drug abusers from seeking cocaine, but they will not become a substitute addictive drug.

As used herein, "cocaine abuse" has its conventional meaning, i.e., misuse or addiction of cocaine. Typically, cocaine is taken by a person due to a craving for cocaine generated by its prior use. Cocaine is abused when it is used for gratification, producing effects not required or recommended for therapy. The resultant high use of cocaine produces many serious and adverse side effects. As such, it is highly desirable to reduce the number and/or intensity of episodes in which a person experiences a craving for the substance or, more preferably, to eliminate the craving episodes entirely.

As such, in another aspect, the present invention provides a method of treating cocaine abuse in a human, the method comprising administering to the human a therapeutically effective amount of a compound having the formula

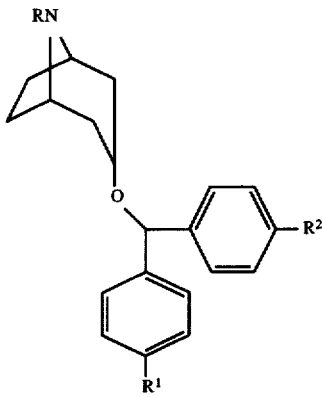

in which: R is a functional group including, but not limited to, hydrogen, alkyl, alkoxy, arylalkyl, aryloxyalkyl, cinnamyl and acyl; and $R^1$ and $R^2$ are independently selected and are functional groups including, but not limited to, hydrogen, alkyl, alkoxy, hydroxy, halogen, cyano, amino and nitro. The previous discussion pertaining to R, $R^1$ and $R^2$ and the preferred embodiments is fully applicable to the benztropine analogs used in the method of treating cocaine addiction and, thus, it will not be repeated again.

"Treatment" or "treating," as used herein, refer to any administration of a compound of the present invention and include: (i) inhibiting the symptoms of the disease, e.g., cocaine addiction; and/or (ii) lessening or inhibiting the long term effects of the disease, e.g., cocaine addiction. In therapeutic applications, compositions are administered to a patient already suffering from the disease, e.g., cocaine addiction, in an amount sufficient to cure or at least partially arrest the symptoms of the disease and its complications. An amount adequate to accomplish this is defined as a "therapeutically effective amount or dose." Amounts effective for this use will depend on the severity and course of the disease, previous therapy, the patient's health status and response to the drugs, and the judgment of the treating physician.

In conjunction with the foregoing method, the present invention provides pharmaceutical compositions comprising a compound of Formula I and a pharmaceutically acceptable diluent, carrier or excipient. The phrase "pharmaceutically or therapeutically acceptable carrier," as used herein, refers to a carrier medium which does not interfere with the effectiveness of the biological activity of the active ingredients and which is not toxic to the host or patient. The pharmaceutical compositions of the present invention can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and parenteral applications, but it will be appreciated that the preferred form will depend on the particular therapeutic application at hand. The methods for the formulation and preparation of therapeutic compositions comprising the compounds of the invention are well known in the art and are described in, for example, REMINGTON'S PHARMACEUTICAL SCIENCES (Mack Publishing Company, Philadelphia, Pa., 17th ed. (1985)), THE MERCK INDEX 11th Ed., (Merck & Co. 1989), and Langer, Science 249: 1527–1533 (1990), the teachings of which are incorporated herein by reference.

The pharmaceutical compositions containing the compounds of the present invention can be administered for therapeutic and/or prophylactic treatments. In therapeutic applications, compositions are administered to a patient already suffering from a disease, e.g., cocaine addiction or Parkinson's disease, in an amount sufficient to cure or at least partially arrest the symptoms of the disease and its complications. An amount adequate to accomplish this is defined as a "therapeutically effective amount or dose." Amounts effective for this use will depend on the severity and course of the disease, previous therapy, the patient's health status and response to the drugs, and the judgment of the treating physician.

In prophylactic applications, the pharmaceutical compositions are administered to a patient susceptible to or otherwise at risk for a particular disease in an amount sufficient to prevent or ameliorate the onset of symptoms. Such an amount is defined as a "prophylactically effective amount or dose." These can be administered orally or by inhalation. In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compounds of the present invention will be in the range of 0.05 to 1000 milligram (mg) per recipient per day, preferably in the range of 0.1 to 100 mg per day. The desired dosage is preferably presented in one, two, three, four or more subdoses administered at appropriate intervals throughout the day. These subdoses can be administered as unit dosage forms, for example, containing 0.01 to 1000 mg, preferably 0.01 to 100 mg of active ingredient per unit dosage form. Again, the desired dosage will depend on, for example, the particular compound employed, the disease to be treated, the manner of administration, the weight and general state of health of the patient, and the judgment of the prescribing physician.

While it is possible to administer the active ingredient of this invention alone, it is preferable to present it as part of a pharmaceutical formulation. The formulations of the present invention comprise at least one compound described herein in a therapeutically or pharmaceutically effective dose together with a pharmacologically acceptable carrier. For parenteral administration, for example, the pharmaceutical compositions comprise a solution of a compound of Formula I, as described above, dissolved or suspended in an acceptable carrier, preferably an aqueous carrier. A variety of aqueous carriers can be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally about 10% to about 95% of the active ingredient and, more preferably, about 25% to about 75% of the active ingredient.

For aerosol administration, the compounds of Formula I are preferably supplied in a finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included as desired, as with, e.g., lecithin, for intranasal delivery.

In addition to the foregoing, the 4',4"-3α-(diphenyhnethoxy)tropane analogs of the present invention are useful as imaging probes for dopamine transporter/cocaine binding sites and as imaging probes for neurodegenerative disorders (e.g., Parkinson's disease). As such, in another aspect, the present invention provides a method of selectively imaging cocaine binding sites of the central nervous system of a human, the method comprising: (a) administering to the central nervous system of the human a compound having the formula

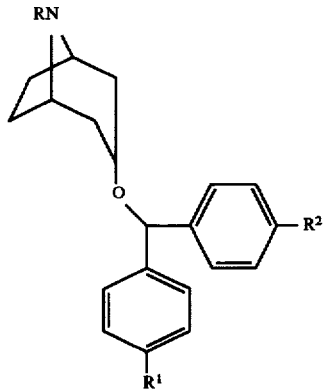

in which: R is a functional group including, but not limited to, hydrogen, alkyl, alkoxy, arylalkyl, aryloxyalkyl, cinnamyl and acyl; and $R^1$ and $R^2$ are independently selected and are functional groups including, but not limited to, hydrogen, alkyl, alkoxy, hydroxy, halogen, cyano, amino and nitro; and (b) detecting the binding of that compound to the central nervous system tissue.

In yet another aspect, the present invention provides a method of detecting or monitoring parkinsonism in a human, the method comprising: (a) administering to the human a detectably labeled compound having the formula

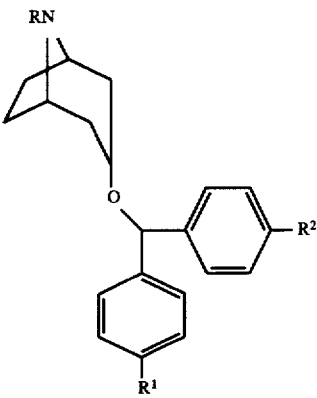

in which: R is a functional group including, but not limited to, hydrogen, alkyl, alkoxy, arylalkyl, aryloxyalkyl, cinnamyl and acyl; and $R^1$ and $R^2$ are independently selected and are functional groups including, but not limited to, hydrogen, alkyl, alkoxy, hydroxy, halogen, cyano, amino and nitro; and (b) detecting the binding of that compound to the central nervous system tissue. Using this method, one can diagnose and/or monitor Parkinson's disease, a neurological disorder characterized by the progressive degeneration of dopamine nerve terminals.

The previous discussion pertaining to R, $R^1$ and $R^2$ and the preferred embodiments is fully applicable to the benztropine analogs used in the method of imaging cocaine binding sites and in the methods of diagnosing/monitoring parkinsonism and, thus, it will not be repeated again. In a presently preferred embodiment, the benztropine analogs of the present invention are labeled with a radioactive or fluorescent label using standard labeling techniques known to and used by those of skill in the art. Suitable labels include, but are not limited to, $^3H$ or $^{11}C$ on the N-linked substituent; $^{123}I$, $^{125}I$ or $^{18}F$ on the diphenylmethoxy group; and $^{99}Tc$ on the diphenylmethoxy group.

In addition, in a presently preferred embodiment, binding of the benztropine analogs to the CNS tissue is detected using positron emission tomography (PET) or single-photon emission computed tomography (SPECT). PET imaging may be carried using any appropriate apparatus, but is preferably carried out using coded single ring positron tomograph (Brownell, et al., *Intl. J. Imaging Syst. Tech.* 1: 207–217, 1989, the teachings of which are incorporated herein by reference). The analog ring design offers a number of advantages for positron tomography. PET imaging can be carried out on conscious human subjects. In addition, SPECT imaging may also be used on human subjects (See, e.g., *Medicine*, Scientific American, Inc., ed. Rubenstein and Federman, 1988; Jaszczak and Coleman, *Invest. Radiol.* 20: 897, 1985; and Coleman, et al., *Invest. Radiol.* 21: 1, 1986, the teachings of which are incorporated herein by reference); preferably SPECT imaging employs gamma-emitting derivatives of the analogs described herein (e.g., benztropine analogs labeled with $^{123}I$ or $^{99}Tc$).

As such, using the benztropine analogs of the present invention, one can (1) assay cocaine receptors in chronic cocaine users and in individuals exposed to cocaine prenatally, (2) assay the receptor occupancy of potential cocaine therapeutics, (3) assay cocaine receptors in individuals that abuse other drugs, (4) investigate the mechanism by which cocaine and related drugs alter behavior, (5) elucidate the receptor properties of the dopamine transporter receptor complex, (6) study the mechanism of dopamine transport, etc. Thus, the benztropine analogs of the present invention are useful, inter alia, in research, e.g., in in vivo and in vitro experiments, to study dopamine transport, the dopamine transport receptor and, in particular, cocaine binding sites.

The invention will be described in greater detail by way of specific examples. The following examples are offered for illustrative purposes, and are intended neither to limit or define the invention in any manner.

EXAMPLES

A. General Methodology

All melting points were determined on a Thomas-Hoover melting point apparatus and are uncorrected. The $^1$H and $^{13}$C NMR data were recorded on a Bruker (Billerica, Mass) AC-300 instrument. Samples were dissolved in an appropriate deuterated solvent. Proton chemical shifts are reported as parts per million (δ) relative to tetramethylsilane (Me$_4$Si; 0.00 ppm) which was used as an internal standard. Carbon chemical shift values (δ) are reported in parts per million (ppm) relative to deuterated chloroform (CDCl$_3$; 77.0 ppm). Mass spectra were recorded on a Hewlett Packard (Palo Alto, Calif.) 5971A mass selective ion detector in the electron-impact mode with sample introduction via a HP-5890 series II, gas chromatograph fitted with an HP-1 (crosslinked methyl silicone gum) 25 meters×0.2 mm i.d., 50 micron film thickness. Ultrapure grade helium was used as the carrier gas at a flow rate of 1.2 ML/min. The injection port and transfer line temperatures were 250° C. and 280° C., respectively. The initial oven temperature was 100° C., held for 3.0 min, programmed to 295° C. at 15.0° C./min, maintained at 295° C. for 10.0 min. Infrared spectra were recorded in KBr with a Perkin-Elmer 1600 Series FTIR. Microanalyses were performed by Atlantic Microlab, Inc. (Norcross, Ga.) and agree within 0.4% of calculated values. TLC solvent used was CHCl$_3$/MeOH/NH$_4$OH; 90:10:1, unless otherwise indicated. All chemicals and reagents were purchased from Aldrich Chemical Co. or Lancaster Synthesis, Inc.

B. Synthesis of 3α-(Diphenylmethoxy)tropanes (7a–q)—General Method

The benzhydrol (4d–4q, 11 mmol) was dissolved in 10 mL SOCl$_2$, at 0° C., under an atmosphere of argon. The reaction mixture was warmed to reflux and allowed to stir at this temperature for 2–18 h. The reaction flask was cooled in an ice bath and the volatiles were removed in vacuo. Addition of dry toluene (2×5 mL) and removal in vacuo ensured the complete removal of SOCl$_2$. The resulting viscous oil was determined spectroscopically to be the desired alkyl chloride. The benzhydrylchloride (crude 5d–5q or commercially available 5a–c) was directly added dropwise to a tropine (1.41 g, 10 mmol) melt (160° C. oil bath) over 2 min. Evolution of HCl gas over 3–30 min resulted in a bronze oil which solidified to a glass upon cooling. The crude product was dissolved in 25 mL CHCl$_3$ and transferred to a separatory funnel. Ion pairing of the desired product was achieved by extraction with 2.8N HCl (2×25 mL, to remove residual tropine), followed by washing the aqueous fraction with CHCl$_3$ (2×10 mL). The combined organic fractions were evaporated to an off-white foam which was recrystallized to give the pure product as the HCl salt (21–83% yield).

C. Synthesis of 3α-4'-Hydroxy-(diphenylmethoxy)tropane (7r)

3α-4'-Benzyloxy(diphenylmethoxy)tropane hydrochloride (synthesized via the general method reported above in 41% yield) (1.0 g, 2.22 mmol) was dissolved in absolute methanol (100 mL) and reduced (H$_2$, 30 psi) over 10% palladium on activated carbon for 3.5 hours. After removal of the catalyst via filtration through celite, the solvent was evaporated in vacuo leaving 0.74 g (95% yield) of a white solid residue which was recrystallized from methanol. Anal. (C$_{21}$H$_{25}$NO$_2$HCl) C, H, N.

D. Synthesis of Pseudotropine (9)

Tropinone (3.0 g, 21.6 mmole) was placed in a dry 250 mL round bottom flask, purged with argon. Anhydrous THF (75 mL, w/o stabilizer) was added and the solution was cooled in a dry ice/acetone bath to −78° C. In another dry, argon purged flask LiBH$_4$ (1.41 g, 64.6 mmole) was dissolved in anhydrous THF (50 mL) and cooled to −78° C. The contents of this flask was transferred to the first flask via cannula, under argon. This flask was rinsed once with additional THF (25 mL). The reaction was allowed to proceed for 6 hours at −78° C. and then warmed gradually to room temperature overnight. The reaction mixture was cooled in an ice water bath and carefully quenched with H$_2$O (10 mL) followed by neutralization with 2.8N HCl. The volatiles were removed in vacuo and the residue was taken up in 1N HCl (100 mL) and heated to reflux for 60 min to dissociate the pseudotropine-boron complex formed. The acidic solution was adjusted to pH=10–11 with 15% NaOH and extracted with CHCl$_3$/2-propanol (3:1, 10×50 mL). The organic fractions were combined, dried over anhydrous Na$_2$SO$_4$, filtered, and concentrated in vacuo resulting in 2.58 g (85% yield) of a white solid product. Recrystallization from toluene/pet ether gave small white needles, mp 106°–109° C. (mp 109° C., The Merck Index, 11th Edition, 1989, #7937, p. 1259).

E. Synthesis of 3β-4'-Chloro-(diphenylmethoxy)tropane (10)

2-Chlorobenzhydrylchloride (8.5 mmol) was added to a pseudotropine (8.5 mmol, free base) melt as described for compounds 7a–q (160° C. oil bath) and allowed to stir at this temperature for 1 h. The crude product was worked up in the same way as described above resulting in an off-white foam which was recrystallized from acetone to give pure 10 as the HCl salt (31% yield), mp 124°–126° C. Anal. (C$_{21}$H$_{25}$NOCl$_2$·0.25H$_2$O): C, H, N.

F. Representative Spectral Data

Compound 7a: $^1$H-NMR (300 MHz, CDCl$_3$); δ1.82–1.89 (m, 4H, H-2,4$_{ax, eq}$), 1.94–1.97 (m, 2H, H-6,7$_{exo}$), 2.08–2.12 (m, 2H, H-6,7$_{endo}$), 2.24 (s, $^3$H, N-CH$_3$), 3.07 ( br t, 2H, H-1,5), 3.54 (t, J=4.6 Hz, 1 H, H-3$_{eq}$), 5.37 (s, 1H, Ph-CH-Ph), 7.20–7.31 (m, 9H, H-aromatics). $^3$C-NMR (75 MHz, CDCl$_3$): δ25.79 (t, C-6,7), 36.17 (t, C-2,4), 40.89 (q, CH$_3$-N), 60-13 (d, C-1,5), 69.25 (d, C-3), 79.89 (d, C-9), 127.42, 128.16, 128.43, 128.48, 128.80 (d, C-protonated aromatic), 132.74, 141.58, 142.43 (s, C-non-protonated aromatic). IR (KBr): 697, 735 (aro-H out of plain), 826, 1043, 1079 (R-0-R), 1320, 1401, 1449, 1484, 1590 (aro. db. stretch) 2525 cm$^{-1}$ (tertiary amine HCl). EIMS: 341 m/z (parent ion, 1%, with isotopic abs for Cl at 343), 235 (10%), 201 (15%), 165 (20%), 140 (100%, base), 124 (40%), 83 (82%), 82 (50%).

Compound 10: $^1$H-NMR (300 MHz, CDCl$_3$): β1.31–1.38 (m$_1$ 2H, H-6,7$_{endo}$), 1.72–1.80 (m$_1$ 4H, H-2,4$_{ax,eq}$), 1.87–1.94 (m$_1$ 2H, H-6,7$_{exo}$), 2.23 (s, $^3$H, N-CH$_3$), 3.15 (brs, 2H, H-1,5), 3.62 (pentet, J=7 Hz, 1 H, H-3$_{ax}$), 5.44 (s, 1H, Ph-CH-Ph), 7.20–7.33 (m$_1$ 9H, H-aromatics). $^{13}$C-NMR (75 MHz, CDCl$_3$): δ26.70 (t, C-6,7), 36.18 (t, C-2,4), 38.17 (q, CH$_3$-N), 59.94 (d, C-1,5), 69.25 (d, C-3), 79.40 (d, C-9), 126.80, 127.87, 128.23, 128.57, 128.77 (d, C-protonated aromatic), 133.26, 140.77, 141.60 (s, C-non-protonated aromatic). IR (KBr): 697, 735 (aro-H out of plain, 1008, 1055, 1079, 1085 (R-O-R), 1402, 1448, 1484, 1590 (aro. db.

stretch) 2543 cm$^{-1}$ (tertiary amine HCl). EIMS: 341 m/z (parent ion, 1%, with isotopic abs. for Cl at 343), 235 (5%), 201 (15%), 165 (20%), 140 (9%), 125 (100%, base) 96 (20%), 83 (90%), 82 (50%).

I. Pharmacology

1. Dopamine Transporter Binding Assay

Male Sprague-Dawley rats (200–250 g, Taconic, Germantown, N.Y.) were decapitated and their brains removed to an ice-cooled dish for dissection of the caudate putamen. The tissue was homogenized in 30 volumes ice-cold modified Krebs-HEPES buffer (15 mM HEPES, 127 mM NaCl, 5 mM KCl, 1.2 mM MgSO$_4$, 2.5 mM CaCl$_2$, 1.3 mM NaH$_2$PO$_4$, 10 mM D-glucose, pH adjusted to 7.4) using a Brinkman polytron and centrifuged at 20,000×g for 10 min at 4° C. The resulting pellet was then washed two more times by resuspension in ice-cold buffer and centrifugation at 20,000×g for 10 min at 4° C. Fresh homogenates were used in all experiments.

Binding assays were conducted in modified Krebs-HEPES buffer on ice. The total volume in each tube was 0.5 mL and the final concentration of membrane after all additions was 0.5% (w/v) corresponding to 200–300 mg of protein/sample. Triplicate samples of membrane suspension were preincubated for 5 min in the presence or absence of the compound being tested. [$^3$H]WIN 35,428 (2-β-carbomethoxy-3-β-(4-fluorophenyl)tropane 1,5-naphthalene disulfonate; specific activity 82.4 Ci/mmol, from New England Nuclear, Boston, Mass., final concentration 1.5 nM) was added and the incubation was continued for 1 hr on ice. The incubation was terminated by the addition of 3 mL of ice-cold buffer and rapid filtration through Whatman GF/B glass fiber filter paper (presoaked in 0.1% BSA in water to reduce non-specific binding) using a Brandee Cell Harvester (Gaithersburg, Md.). The filters were washed with three additional 3 mL washes and transferred to scintillation vials. Absolute ethanol (0.5 mL) and Beckman Ready Value Scintillation Cocktail (2.75 mL) were added to the vials which were counted the next day at an efficiency of about 36%. Under these assay conditions, an average experiment yielded approximately 6,000 dpm total binding per sample, and approximately 250 dpm non-specific binding, defined as binding in the presence of 100 µM cocaine. Each compound was tested with concentrations ranging from 0.01 nM to 100 µM for competition against binding of [$^3$H]WIN 35,428, in three independent experiments, each performed in triplicate.

2. [$^3$H]Dopamine Uptake Assay

Rats were sacrificed by decapitation and their brains removed to an ice-cooled dish for dissection of the caudate putamen. [$^3$H]Dopamine uptake was measured in a chopped tissue preparation as described previously (Izenwasser, S., et al., *Brain Res.* 1990, 520, 303–309). Briefly, the tissue was chopped into 225 µm slices on a McIllwain tissue slicer with two successive cuts at an angle of 90°. The strips of tissue were suspended in oxygenated modified Krebs-HEPES buffer (see, above), which was pregassed with 95% O$_2$/5% CO$_2$ and warmed to 37° C. After rinsing, aliquots of tissue slice suspensions were incubated in buffer in glass test tubes at 37° C. to which either the drug being tested or no drug was added, as appropriate. After a 5 min incubation period in the presence of drug, [$^3$H]dopamine (final concentration 15 nM, specific activity 50 Ci/mmol, from Amersham Corp, Arlington Heights, Ill.) was added to each tube. After 5 min, the incubation was terminated by the addition of 2 mL of ice-cold buffer to each tube and filtration under reduced pressure over glass fiber filters (presoaked in 0.1% polyethylenimine in water). The filters were rinsed and placed in scintillation vials to which 1 mL methanol and 2 mL 0.2 M HCl were added to extract the accumulated [$^3$H]dopamine. Radioactivity was determined by liquid scintillation spectrometry at an efficiency of approximately 30%. The reported values represent specific uptake from which non-specific binding to filters was subtracted.

3. Locomotor Activity Assay

Ambulatory activity of Male Swiss Webster mice (Taconic Farms) were studied in 40 cm$^3$ clear acrylic chambers. The acrylic chambers were placed inside monitors (Omnitech Electronics, Columbus, Ohio) that were equipped with light sensitive detectors, spaced 2.5 cm apart along two perpendicular walls. Mounted on the opposing walls were infrared light sources that were directed at the detectors. One count of horizontal activity was registered each time the subject interrupted two successive beams. Repetitive interruptions of the same beam due to behaviors, such as head bobbing or grooming, were not counted. Mice were injected and immediately placed in the apparatus for 60 min. Injections were administered i.p. in volumes of 1 mL/100 g. Each dose was studied in eight mice, and mice were used only once.

Horizontal activity counts are shown for the first 30 min of the session in which the maximal stimulation of activity was obtained. Each dose-effect curve was analyzed using standard analysis of variance (ANOVA) and post-hoc testing determine significance of effects at individual doses.

4. Drug Discrimination Assay

Six adult male Sprague-Dawley rats (Charles River, Wilmington, Mass.) were maintained at 350 g by post-session feeding. All subjects had unrestricted access to water within a temperature-controlled animal housing room under a 12 h light/dark cycle. All testing was conducted during the light phase.

Rats were studied in operant conditioning test chambers (BRS/LVE, Model RTC-022, Laurel, Md.) which contained two response keys. Responses were recorded as depressions of the keys with a downward force of 0.2N. Each response produced an audible click when the house light and the stimulus lamps over either lever were illuminated.

Experimental sessions were conducted at approximately the same time daily, five days per week. Before each training session, subjects received either saline or cocaine (10 mg/kg, i.p.) which were given in a mixed sequence. When Subjects received cocaine, they were trained with food reinforcement to emit 20 consecutive responses on only one of the two response keys. Food presentation was followed by a 20-sec time out period during which all stimulus lights were out and responses had no scheduled consequences. When subjects received saline, responses on the alternate key produced a food pellet according to the same schedule. Injections were given 5 min before sessions started. Sessions ended after 20 food presentations or 15 min, whichever occurred first. Since subjects had been trained previously, no further training was necessary prior to conducting test sessions, in which the effects of various doses of cocaine or test compounds were examined. Test sessions were conducted after each two training sessions and were identical to those training sessions with the exception that 20 consecutive responses on either of the response keys produced a food pellet. Subjects were injected i.p. with one of several doses of cocaine or test compound. Each dose was typically examined once in each subject. Test sessions were conducted if subjects met criteria of emitting greater than 85% correct responses in the entire session, and before the first food pellet in each of the two training sessions preceding the test session. When subjects failed to meet the criteria, training continued until they did so for two consecutive sessions before testing resumed.

J. PET Imaging

The benztropine analogs of the present invention provide useful PET imaging probes. As previously discussed, PET imaging has at least two applications: (1) to evaluate the time course of accumulation of a candidate cocaine substitute in the brain as well as the duration of receptor occupancy, and (2) to monitor cocaine receptors and dopamine nerve terminals in competitor studies. Benztropine analogs having a high affinity for the dopamine transporter are most useful as PET imaging probes because the dose of radioactivity needed to image a target decreases along with decreases in organ dosimetry. In addition, high affinity benztropine analogs are preferable because dopamine may compete effectively with trace doses of low affinity analogs in vivo, thereby reducing the apparent accumulation in striatum. Affinity of a compound is determined using the in vitro binding assay, and distribution is determined by in vivo and ex vivo receptor autoradiography.

Compounds may also be analyzed for possible in vivo breakdown. Arterial blood samples are withdrawn at predetermined intervals, plasma separated by centrifugation, basified, extracted with $CH_2Cl_2$, the solvent evaporated, and compound metabolites analyzed by HPLC. The percent of water soluble metabolites in the plasma residue is determined by radioactive monitoring and analyzed by HPLC. After appropriate corrections for decay, sensitivity, uniformity and attenuation, the collected image data is reconstructed for tissue concentration maps using a Hanning windowed filtered backprojection. The tissue concentration maps are combined with arterial plasma data to calculate receptor uptake using the model developed by Patlak et al., (Blood Flow Metab. 5: 584, 1986). This model relies on the hypotheses (1) that the specific binding of [$^{11}C$]radioligand to striatal membranes can be considered as irreversible for the duration of the PET study; and (2) that non-specific ligand binding is distributed evenly through the brain and can be determined from the activity in the cerebellum.

Arterial blood sampling of the monkey will be taken for the same period of time to determine the arterial blood activity curve. The brain distribution, striatum:cerebellar ratio as a function of time and the blood levels of the compound are performed in three monkeys. The following steps are used to evaluate model parameters. 1) Time course of plasma radioactivity is determined. 2) Plasma curves are corrected for metabolism of the tracer and a biexponential function (Gauss-Newton algorithm/non-linear curve-fitting) is fit to the data. 3) From dynamic PET images, time activity curves for striatum, occipital cortex and cerebellum are obtained. 4) The plasma activity of the tracer at the time of PET measurements is determined. 5) The corrected plasma curve at the time of the PET measurements is integrated. 6) The tissue activity ratio (t) [Striatum/Cerebellum]=f [integrated plasma activity (t)/plasma activity (t)] is determined. Initially striatum:cerebellar ratios are calculated as a function of time. The compounds with the highest striatal concentration, fastest blood clearance, least metabolism and least non-specific binding are most preferable in the invention.

Prior to PET imaging studies, test animals are subjected to one magnetic resonance imaging (MRI) to determine stereotaxic coordinates of regions of interest using a stereotaxic head holder designed for these studies. The anaesthetized animal (ketamine 10–20 mg/kg/; xylazine 1–2 mg/kg) is placed on the computer controlled imaging table face down. The head is placed into a stereotaxic head holder and the table is moved until the plane of interest is positioned in the imaging field. Two planes of interest are selected, the caudate-putamen and the cerebellum and the selected brain levels are imaged sequentially. Generally, the compound (for example, [$^{11}C$]CFT (400–2,000 Ci/mmol; approximately 1–5 nmoles) is administered to control monkeys and the regional brain distribution association and dissociation rates determined. Following rapid intravenous injection of the compound, dynamic imaging in the selected brain level is started; 30 s scans for 5 min, 1 min scans for next 10 min, 2 min scans for 45 min and 5 min scans thereafter for 30 min. Arterial blood samples of 0.25–0.5 $m_1$ for determination of radioactivity and 1.2 $m_1$ (*) for determination of lipophilic metabolites by H.P.L.C. are collected according the following time table; 0, 15" 30", 45", 60" (*), 75", 90", 105", 120", (*),5'(*), 10'(*), 15', 20', 30'(*), 45', 60'(*), 75', 90'(*). Plasma and total blood radioactivity are counted in a well counter that is cross calibrated with the tomograph.

PET imaging may be carried but using any appropriate apparatus, but is preferably carried out using coded single ring positron tomograph (Brownell, et al., Intl. J. Imaging Syst. Tech. 1: 207–217, 1989). PET imaging can also be carried out on conscious human subjects using the procedure described above. In addition, SPECT imaging may also be used on human subjects (See, e.g., Medicine, Scientific American, Inc., ed. Rubenstein and Federman, 1988; Jaszczak and Coleman, Invest. Radiol. 20: 897, 1985; and Coleman, et al., Invest. Radiol. 21: 1, 1986, the teachings of which are incorporated herein by reference); preferably SPECT imaging employs gamma-emitting derivatives of the analogs described herein (e.g., benztropine analogs labeled with $^{123}I$ or $^{99}Tc$).

K. Analysis of Data

Saturation and displacement data were analyzed by the use of the nonlinear least squares curve-fitting computer program LIGAND (Munson, P. J., et al., Anal. Biochem. 1980, 107, 220–239). Data from replicate experiments were modeled together to produce a set of parameter estimates and the associated standard errors of these estimates. In each case, the model reported fit significantly better than all others according to the F test at p<0.05. The $K_i$ values reported are the dissociation constants derived for the unlabeled ligands. Uptake data were analyzed using standard, analysis of variance and linear regression techniques (Snedecor, G. W., et al., Statistical Methods, 6th ed. Iowa State University Press, Ames Iowa, 1967, pp. 135–171). $IC_{50}$ values were calculated using the linear portion of the concentration-response curve (linear regression p<0.05).

In both saturation and competition experiments, two components of [$^3H$]WIN 35,428 binding were apparent. Analysis of the data utilizing the LIGAND program revealed a high affinity component with a $K_D$ of 7±5 nM and a $B_{max}$ of 445±338 fmol/mg protein and a low affinity component with a $K_D$ of 126±115 nM and a $B_{max}$ of 1995±559 fmol/mg protein. Competition of [$^3H$]WIN 35,428 binding by cocaine also revealed two binding sites (see, Table 2).

Serotonin (5-HTT), norepinephrine transporter (NET) and muscarinic $m_1$ and $m_2$ receptor binding data were provided by NOVASCREEN. The radiolabeled ligands used and the methods were from the following published procedures: 5-HTT: [$^3H$]citalopram (specific activity 70–87 Ci/mmol, final ligand concentration 0.7 nM) (D'Amato, R. J., et al., J. Pharmaco. Exp Ther. 1987, 242, 364–371); NET: [$^3H$]desmethylimipramine (specific activity 40–70 Ci/mmol, final ligand concentration 3.0 nM) (Raisman, R., et al., Eur. J. Pharmacol. 1982, 78, 345–351); muscarinic $m_1$ receptors: [$^3H$]pipenzepine (specific activity 70–87 Ci/mmol, final ligand concentration 1.0 nM) (Watson, J. Pharmacol. Exp. Ther. 1986, 237, 419–427); muscarinic $m_2$ receptors: [$^3H$]

AFDX 384 (specific activity 70–120 Ci/mmol, final ligand concentration 5.0 nm) (Hammer, R., et al., *Life Sci.* 1986, 38, 1653–1662).

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A compound having the formula

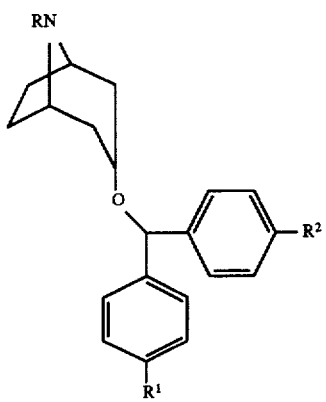

in which:

R is a member selected from the group consisting of hydrogen, alkyl, alkoxy, arylalkyl, aryloxyalkyl, cinnamyl and acyl; and $R^1$ and $R^2$ are members independently selected from the group consisting of hydrogen, alkyl, alkoxy, hydroxy, halogen, cyano, amino and nitro;

with the provisos:

if R is methyl, $R^1$ and $R^2$ are not both Cl;

if R is methyl, $R^1$ and $R^2$ are not both F;

if R is methyl and $R^1$ is Cl, $R^2$ is not hydrogen; and if R is methyl, $R^1$ and $R^2$ are not not hydrogen.

2. The compound in accordance with claim 1 wherein

R is methyl;

$R^1$ is methoxy; and $R^2$ is selected from the group consisting of hydrogen and methoxy.

3. The compound in accordance with claim 1 wherein

R is methyl;

$R^1$ is nitro; and $R^2$ is hydrogen.

4. The compound in accordance with claim 1 wherein

R is methyl;

$R^1$ is cyano; and $R^2$ is hydrogen.

5. The compound in accordance with claim 1 wherein

R is methyl;

$R^1$ is Br; and $R^2$ is selected from the group consisting of hydrogen, Br, Cl and F.

6. The compound in accordance with claim 1 wherein

R is methyl;

$R^1$ is F; and $R^2$ is selected from the group consisting of hydrogen, Br and Cl.

7. The compound in accordance with claim 1 wherein

R is methyl;

$R^1$ is an alkyl selected from the group consisting of methyl, ethyl, propyl, butyl, i-butyl, t-butyl, pentyl and hexyl; and $R^2$ is selected from the group consisting of hydrogen and alkyl.

8. The compound in accordance with claim 1 wherein

R is methyl;

$R^1$ is hydroxy; and $R^2$ is selected from the group consisting of hydrogen, hydroxy, F, Br and Cl.

9. The compound in accordance with claim 1 wherein

R is alkyl; and $R^1$ and $R^2$ are independently selected from the group consisting of Br, Cl, F and I.

10. The compound in accordance with claim 1 wherein

R is N-cinnamyl; and $R^1$ and $R^2$ are independently selected from the group consisting of Br, Cl, F and I.

11. The compound in accordance with claim 1 wherein

R is arylalkyl; and $R^1$ and $R^2$ are independently selected from the group consisting of Br, Cl, F and I.

12. A pharmaceutical composition comprising a pharmaceutically acceptable excipient and a compound having the formula

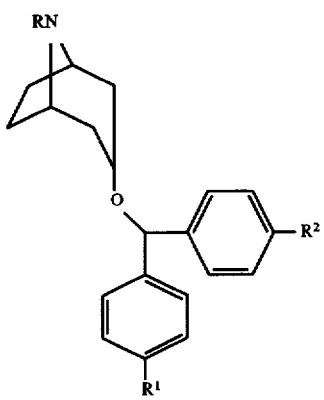

in which:

R is a member selected from the group consisting of hydrogen, alkyl, alkoxy, arylalkyl, aryloxyalkyl, cinnamyl and acyl; and $R^1$ and $R^2$ are members independently selected from the group consisting of hydrogen, alkyl, alkoxy, hydroxy, halogen, cyano, amino and nitro with the proviso:

if R is methyl, $R^1$ and $R^2$ are not both hydrogen.

13. A method of treating cocaine addition in a human, said method comprising administering to said human a therapeutically effective amount of a compound having the formula

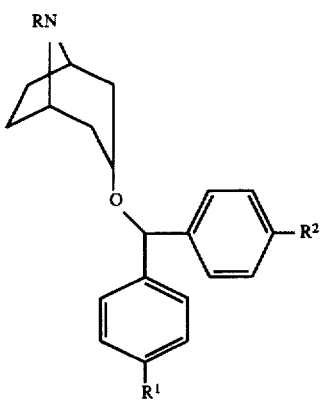

in which:

R is a member selected from the group consisting of hydrogen, alkyl, alkoxy, arylalkyl, aryloxyalkyl, cinnamyl and acyl; and R¹ and R² are members independently selected from the group consisting of hydrogen, alkyl, alkoxy, hydroxy, halogen, cyano, amino and nitro with the proviso;

if R is methyl, R¹ and R² are not both hydrogen.

14. The method in accordance with claim 13 wherein
R is methyl; and
R¹ and R² are both F.

15. The method in accordance with claim 13 wherein
R is methyl; and
R¹ and R² are both Cl.

16. The method in accordance with claim 13 wherein
R is alkyl;
R¹ is Br; and
R² is selected from the group consisting of hydrogen, Br, Cl and F.

17. A method for preparing a compound having the formula

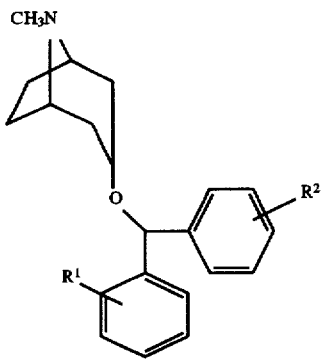

(II)

in which R¹ and R² are members independently selected from the group consisting of hydrogen, alkyl, alkoxy, hydroxy, halogen, cyano, amino and nitro, said method comprising:

(a) providing a benzhydrylhalide having the formula

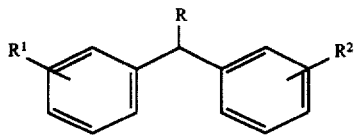

in which:

R is a member selected from the group consisting of Br, Cl, F and I; and

R¹ and R² are members independently selected from the group consisting of hydrogen, alkyl, alkoxy, hydroxy, halogen, cyano, amino and nitro;

(b) adding said benzhydrylhalide to a tropine at a temperature of about 140° C. to about 180° C. to form a reaction mixture; and (c) recovering the compound of Formula II from said reaction mixture.

18. The method in accordance with claim 17 wherein

R is Cl;

R¹ and R² are members independently selected from the group consisting of H, Br, Cl, F and I.

19. The method in accordance with claim 17 wherein said benzhydrylhalide is added to said tropine at a temperature of about 150° C. to about 170° C.

20. The method in accordance with claim 17 wherein step (c) further comprises the steps of:

(i) extraction with aqueous HCl to remove residual tropine;

(ii) washing the aqueous fraction with CHCl₃ and combining the organic fractions; and (iii) evaporating the organic fractions to obtain the compound of Formula II.

* * * * *